(12) United States Patent
Casey et al.

(10) Patent No.: US 11,957,855 B2
(45) Date of Patent: Apr. 16, 2024

(54) BALLOON GUIDE CATHETER WITH POSITIVE VENTING OF RESIDUAL AIR

(71) Applicant: Neuravi Limited, Galway (IE)

(72) Inventors: Brendan Casey, Galway (IE); Karl Keating, Galway (IE); Ronald Kelly, Cannistown (IE)

(73) Assignee: NEURAVI LIMITED, Galway (IE)

( * ) Notice: Subject to any disclaimer, the term of this patent is extended or adjusted under 35 U.S.C. 154(b) by 606 days.

(21) Appl. No.: 16/601,256

(22) Filed: Oct. 14, 2019

(65) Prior Publication Data
US 2020/0353228 A1    Nov. 12, 2020

Related U.S. Application Data

(60) Provisional application No. 62/845,683, filed on May 9, 2019, provisional application No. 62/845,711, filed
(Continued)

(51) Int. Cl.
*A61M 25/10* (2013.01)

(52) U.S. Cl.
CPC .. *A61M 25/10184* (2013.11); *A61M 25/1034* (2013.01); *A61M 2025/1056* (2013.01); *A61M 2025/1077* (2013.01)

(58) Field of Classification Search
CPC .... A61M 25/10184; A61M 2025/1077; A61M 2025/0037; A61M 2025/004;
(Continued)

(56) References Cited

U.S. PATENT DOCUMENTS 4,323,071 A * 4/1982 Simpson ........... A61M 25/1036
                                                         604/920
4,684,363 A    8/1987 Ari et al.
(Continued)

FOREIGN PATENT DOCUMENTS

JP    2016168151    9/2016
WO    2007139799    12/2007
(Continued)

OTHER PUBLICATIONS

Co-Pending, co-owned, U.S. Appl. No. 16/601,185, filed Oct. 14, 2019.
(Continued)

*Primary Examiner* — Darwin P Erezo
*Assistant Examiner* — Brigid K Byrd
(74) *Attorney, Agent, or Firm* — TROUTMAN PEPPER HAMILTON SANDERS LLP

(57) ABSTRACT

A balloon guide catheter including a catheter shaft having a main lumen defined therein extending axially therethrough to receive a guidewire therein and an inflation lumen defined axially therein arranged semi-encircling the main lumen. The inflation lumen having an inlet port radially outward from the catheter shaft and an exhaust vent(s) disposed proximate the distal end of the catheter shaft. The exhaust vent(s) being disposed longitudinally through a distal terminating end of the inflation lumen or radially inward in fluid communication with the main lumen. A porous membrane is disposed at the exhaust vent(s) to permit only gas to pass therethrough. Secured about the outer surface proximate the distal end of the catheter shaft and coinciding with the inlet port is a balloon.

11 Claims, 15 Drawing Sheets

Related U.S. Application Data on May 9, 2019, provisional application No. 62/845,747, filed on May 9, 2019, provisional application No. 62/845,699, filed on May 9, 2019.

(58) Field of Classification Search
CPC ........ A61M 2025/1043; A61M 25/104; A61M 25/10; A61B 17/12109; A61B 17/12136; A61B 2017/22067
See application file for complete search history.

(56) References Cited

U.S. PATENT DOCUMENTS

| | | | |
|---|---|---|---|
| 4,715,378 A | 12/1987 | Pope, Jr. et al. | |
| 4,753,238 A | 6/1988 | Gaiser | |
| 4,793,351 A | 12/1988 | Landman et al. | |
| 4,811,737 A | 3/1989 | Rydell | |
| 4,821,722 A | 4/1989 | Miller et al. | |
| 5,035,705 A | 7/1991 | Burns | |
| 5,100,385 A | 3/1992 | Bromander | |
| 5,135,486 A * | 8/1992 | Eberle | A61M 25/104 604/103.1 |
| 5,176,698 A * | 1/1993 | Burns | A61M 25/104 606/192 |
| 5,224,933 A | 7/1993 | Bromander | |
| 5,256,143 A * | 10/1993 | Miller | A61M 29/02 606/192 |
| 5,800,421 A | 9/1998 | Lemelson | |
| 6,102,891 A | 8/2000 | Maria van Erp | |
| 6,102,931 A | 8/2000 | Thornton | |
| 6,709,429 B1 | 3/2004 | Schaefer et al. | |
| 6,811,559 B2 | 11/2004 | Thornton | |
| 6,953,431 B2 | 10/2005 | Barthel | |
| 6,994,687 B1 | 2/2006 | Shkolnik | |
| 7,160,266 B2 | 1/2007 | Shkolnik | |
| 7,338,511 B2 | 3/2008 | Mirigian et al. | |
| 7,678,075 B2 | 3/2010 | Wantink et al. | |
| 8,298,218 B2 | 10/2012 | Mahrouche | |
| 8,926,560 B2 | 1/2015 | Dinh et al. | |
| 9,155,869 B2 | 10/2015 | Ehrenreich et al. | |
| 9,463,035 B1 | 10/2016 | Greenhalgh et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 10,576,254 B2 | 3/2020 | Yang et al. | |
| 10,682,152 B2 | 6/2020 | Vale et al. | |
| 11,202,891 B2 | 12/2021 | Gulachenski et al. | |
| 2002/0103473 A1 * | 8/2002 | Roychowdhury | A61M 25/10 604/525 |
| 2003/0023204 A1 | 1/2003 | Vo et al. | |
| 2004/0260329 A1 | 12/2004 | Gribbons et al. | |
| 2005/0070881 A1 * | 3/2005 | Gribbons | A61M 25/0052 604/525 |
| 2005/0124932 A1 | 6/2005 | Foster et al. | |
| 2005/0182359 A1 * | 8/2005 | Chin | A61M 25/0075 604/96.01 |
| 2006/0030814 A1 | 2/2006 | Valencia et al. | |
| 2008/0200904 A1 | 8/2008 | Cluff et al. | |
| 2010/0234940 A1 | 9/2010 | Dolan | |
| 2012/0265134 A1 | 10/2012 | Echarri et al. | |
| 2012/0296366 A1 | 11/2012 | Rundquist et al. | |
| 2013/0289549 A1 | 10/2013 | Nash et al. | |
| 2014/0188043 A1 * | 7/2014 | Shibahara | A61M 25/1006 604/96.01 |
| 2014/0257359 A1 | 9/2014 | Tegels et al. | |
| 2015/0032049 A1 | 1/2015 | Hopkinson et al. | |
| 2015/0073467 A1 | 3/2015 | Eaton | |
| 2015/0174363 A1 | 6/2015 | Sutermeister et al. | |
| 2015/0224290 A1 | 8/2015 | Chanduszko et al. | |
| 2016/0001040 A1 | 1/2016 | Yamaguchi et al. | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Grandfield | |
| 2017/0100183 A1 | 4/2017 | Iaizzo et al. | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |

(56) References Cited

U.S. PATENT DOCUMENTS

| | | |
|---|---|---|
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 * | 12/2017 | Guyon ............ A61M 25/10187 |
| 2018/0333192 A1 | 11/2018 | Sliwa et al. |
| 2019/0167287 A1 | 6/2019 | Vale et al. |
| 2019/0359786 A1 | 11/2019 | Trahan et al. |
| 2020/0179657 A1 | 6/2020 | Liu |
| 2020/0246036 A1 | 8/2020 | Kallmes et al. |
| 2022/0143360 A1 | 5/2022 | Kugler et al. |

FOREIGN PATENT DOCUMENTS

| | | |
|---|---|---|
| WO | 2013163254 | 10/2013 |
| WO | 2017192999 | 11/2017 |

OTHER PUBLICATIONS

Co-Pending, co-owned, U.S. Appl. No. 16/601,221, filed Oct. 14, 2019.

Co-Pending, co-owned, U.S. Appl. No. 16/601,202, filed Oct. 14, 2019.

L.E. Romans, "The Use of Contrast Media in the CT Department", CEWebsource.com, May 15, 2013 (50 pp).

* cited by examiner

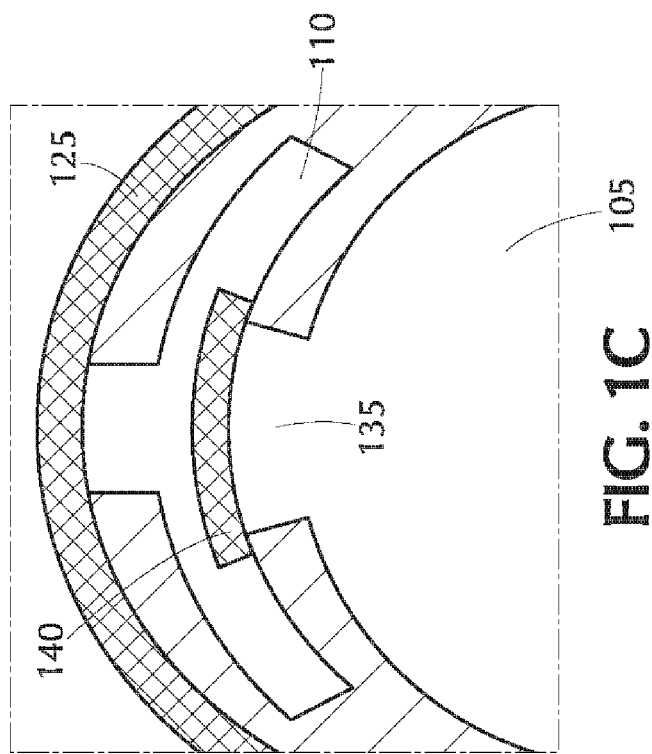
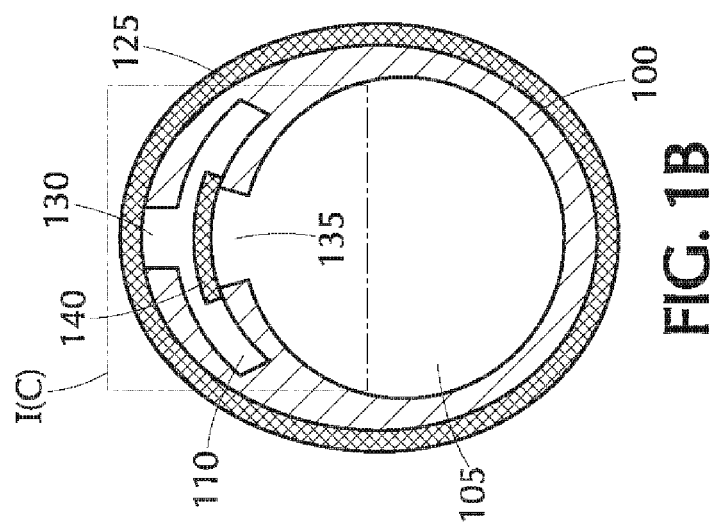

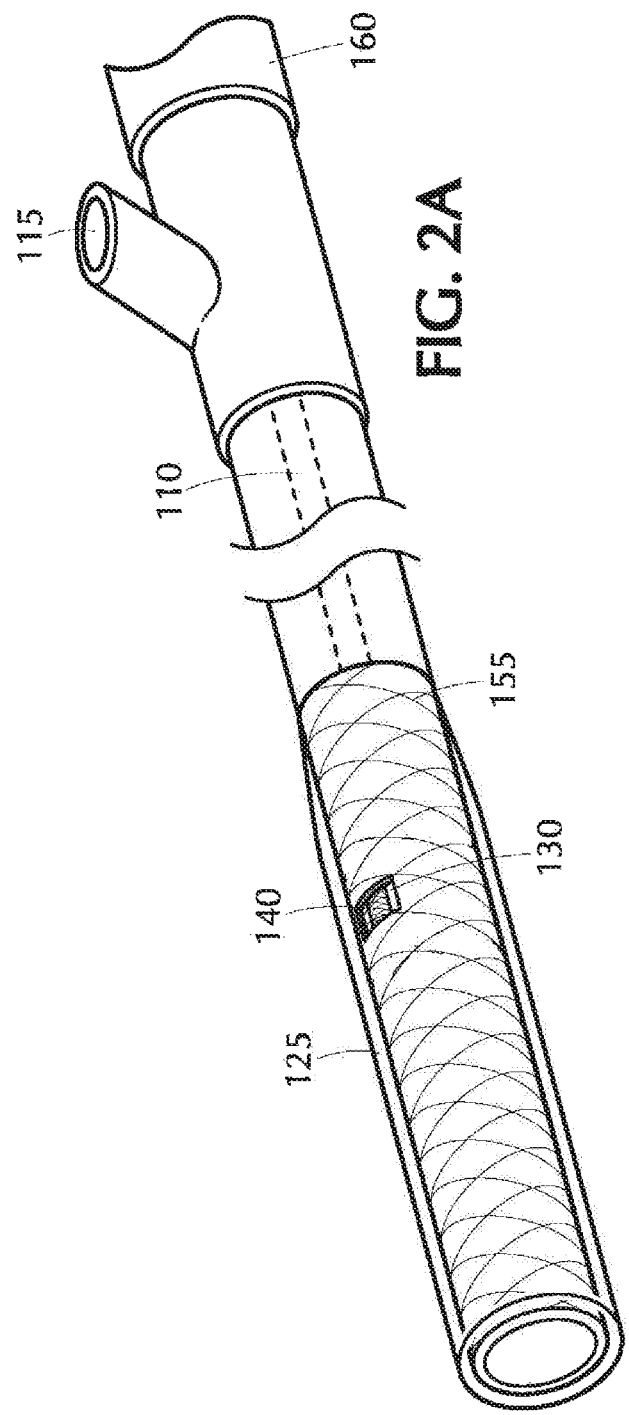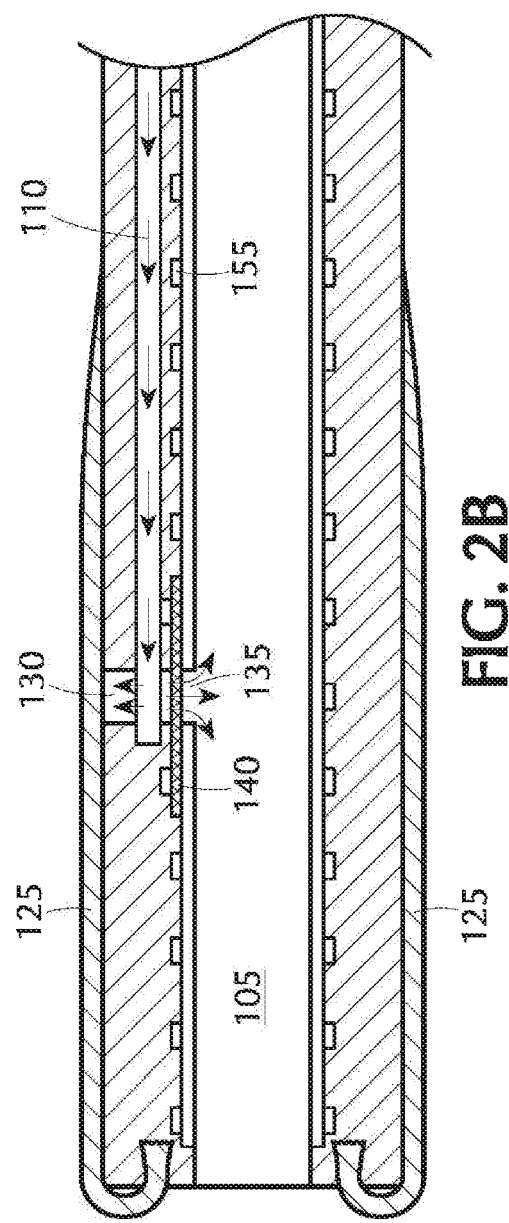

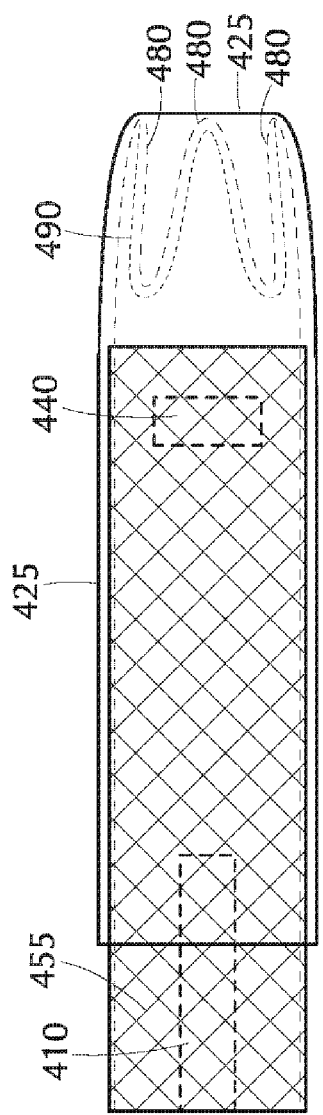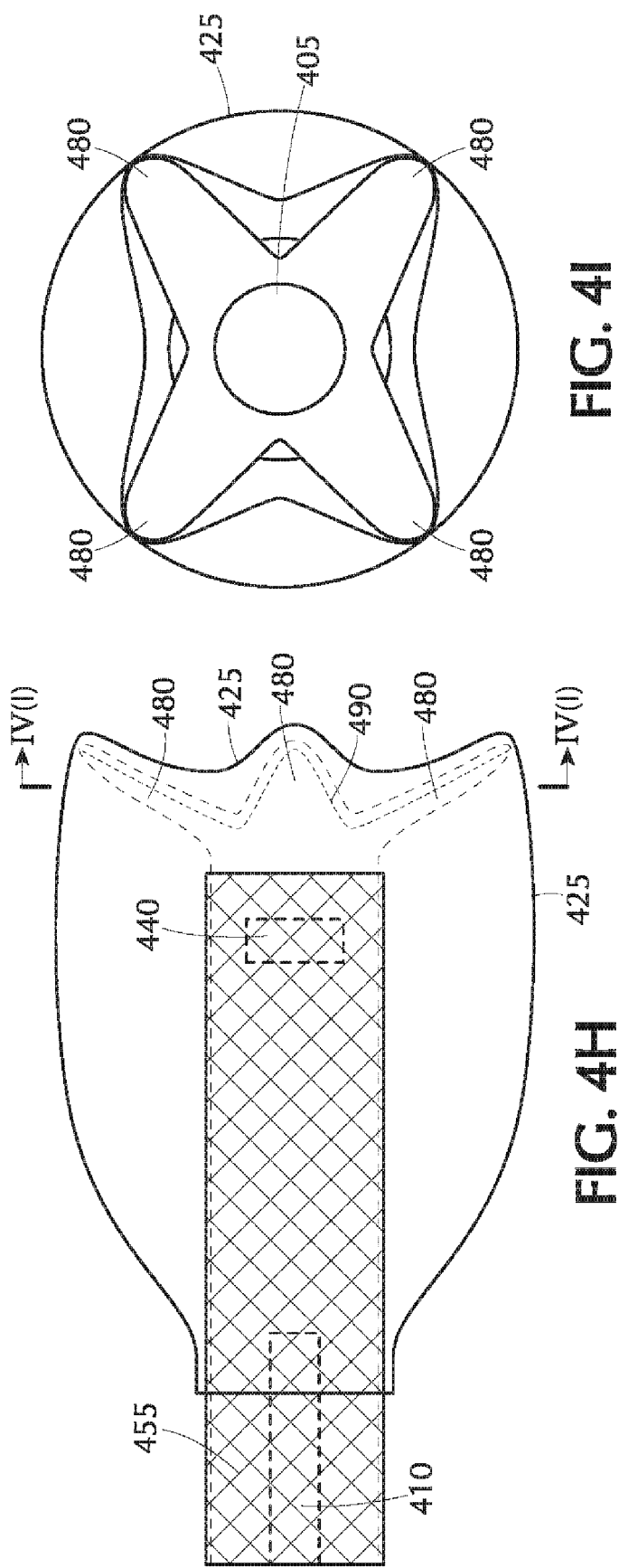

BALLOON GUIDE CATHETER WITH POSITIVE VENTING OF RESIDUAL AIR

CROSS-REFERENCE TO RELATED APPLICATIONS

This application claims the benefit of the following: U.S. Provisional Application No. 62/845,683, filed on May 9, 2019; U.S. Provisional Application No. 62/845,699, filed on May 9, 2019; U.S. Provisional Application No. 62/845,711, filed on May 9, 2019; and U.S. Provisional Application No. 62/845,747, filed on May 9, 2019, each of which is herein incorporated by reference in its entirety.

BACKGROUND OF THE INVENTION

Field of the Invention

The present invention relates to an intravascular medical system. In particular, the present invention is directed to an improved balloon guide catheter with positive venting of residual air trapped therein while being prepped by the physician or interventionalist prior to being introduced into the body.

Description of Related Art

Catheters are widely used today in connection with a variety of intravascular medical procedures or treatments. One such widely adopted use or application of an intravascular catheter is in a thrombectomy medical procedure following an acute ischemic stroke (AIS) in which a sheath guide catheter (non-balloon guide catheter) or balloon guide catheter is introduced into the internal carotid artery to serve as a conduit for ancillary devices such as guidewire(s), microcatheter(s), stentriever(s) or intermediate catheter(s). The sheath guide catheter (non-balloon guide catheter) maintains access to the intended treatment location within a blood vessel and shortens procedural times by facilitating multiple passes with ancillary devices to the treatment location. Use of a balloon guide catheter provides the additional benefit, once inflated to an expanded state, of arresting blood flow and achieving complete apposition of the vessel. The blood flow arrest offers extra security in limiting the blood pressure exerted on the clot as well as maximizing the suction performance during aspiration stage, as the stentriever and/or direct aspiration catheter retracts back into the balloon guide catheter with the captured clot. While such benefits are readily apparent and clinically proven, use of a balloon guide catheter requires somewhat arduous prepping steps be followed in ridding the inflating lumen of residual air to be replaced with inflating medium both in the inflating lumen and the balloon. These prepping steps performed prior to the introduction of the balloon guide catheter into the body deter some physicians or interventionalists from using a balloon guide catheter altogether despite such advantages, instead choosing to employ a sheath guide catheter (non-balloon guide catheter) that doesn't require such prepping steps.

Prior to being introduced into the target vessel of the body, a conventional balloon guide catheter is prepped by the physician or interventionalist following a multi-step process to properly purge residual air trapped therein. This preparatory procedure typically calls for applying a vacuum or negative pressure at an inflation port to remove the residual air, followed immediately thereafter by dispensing of an inflation medium back into the catheter. This inflation lumen vacuum procedure may be required to be repeated multiple times to insure complete expulsion of the residual air. If the purging steps are not followed correctly or skipped over entirely, the residual air in the balloon guide catheter may be exhausted into the blood vessel, in the event of a balloon failure, having a dangerous and harmful effect on the patient.

It is therefore desirable to streamline the number of steps or actions to purge residual air from the balloon guide catheter increasing its desirability and ease of use while optimizing time efficiency as well reducing the potential for human error.

SUMMARY OF THE INVENTION

An aspect of the present invention is directed to an improved balloon guide catheter that minimizes the number of prepping steps or actions to rid the device of residual air.

Another aspect of the present invention relates to an improved balloon guide catheter with positive venting and method for use of such inventive catheter.

Yet another aspect of the present invention is directed to an improved balloon guide catheter in which the location of the exhaust and inflating vents ensures that inflation of the balloon with inflating medium occur only upon full and complete bleeding of the residual air from the inflating lumen.

Still another aspect of the present invention relates to an improved guide catheter in which the inflating medium serves a dual function or purpose, initially to purge the residual air from the inflating lumen and, once bled, thereafter to inflate the balloon.

While yet another aspect of the present invention is directed to an improved balloon guide catheter that when prepped by the physician or interventionalist is visibly verifiable that the balloon has been properly purged of residual air prior to introduction into the patient.

It is yet another aspect of the present invention to provide an improved balloon guide catheter with positive venting in which residual air is purged prior to introduction into the body, thereby eliminating the need for a vacuum or negative pressure during prepping.

An aspect of the present invention is directed to a balloon guide catheter including a catheter shaft having an outer surface, a proximal end, and an opposite distal end. The catheter shaft has a main lumen defined therein extending axially therethrough from the proximal end to the distal end. The main shaft is configured to receive a guidewire therein; the catheter shaft having an inflation lumen defined axially therein arranged semi-encircling the main lumen; the inflation lumen having an inlet port defined radially outward from the catheter shaft and at least one exhaust vent disposed proximate the distal end of the catheter shaft, wherein the at least one exhaust vent being disposed longitudinally through a distal terminating end of the inflation lumen or radially inward in fluid communication with the main lumen. The catheter further includes a porous membrane disposed at the at least one exhaust vent, wherein the porous membrane having a plurality of holes defined therein sized to permit only gas to pass therethrough. In addition, the catheter also has an expandable balloon secured about the outer surface of the catheter shaft proximate the distal end of the catheter shaft and coinciding with the inlet port.

Another aspect of the present invention relates to a method for using a balloon guide catheter, as described in the preceding paragraph. The method includes the step of prior to introduction of the balloon guide catheter into a target vessel, prepping the balloon guide catheter by positively venting residual air distally from the inflation lumen and the expandable balloon via the at least one exhaust vent.

A still further aspect of the present invention is directed to a method of manufacture of a positive distal vented balloon guide catheter. The method including the steps of forming a tubular main liner to form a main lumen axially therethrough; the formed tubular main liner having an etched region and a polymeric strike layer at selected surfaces. A first opening is punched radially through the formed tubular main liner that serves as a radial exhaust vent in fluid communication with the main lumen defined axially therethrough. A provided microporous membrane etched and having a polymeric strike layer at selected sections of both surfaces of the microporous membrane is positioned to cover the punched exhaust vent defined in the formed tubular main liner. The formed tubular main liner is laminated to attached together with the microporous membrane under an application of heat. Thereafter, a polymer jacket is positioned over the laminated assembly including the mandrel, the formed tubular main liner, and the microporous membrane; and heat shrink is applied to cause reflow of the polymer jacket bonding the polymer jacket to the etched/strike layer of the microporous membrane as well as to the etched/strike layer of the formed tubular main liner. In a similar fashion a tubular inflation liner is formed having an inflation lumen axially therethrough; the formed tubular inflation liner having an etched region and a polymeric strike layer at selected surfaces. A second opening s punched radially through the formed tubular inflation liner that serves as a radial exhaust vent in fluid communication with the inflation lumen defined axially therethrough. The second opening of the formed tubular inflation liner is positioned longitudinally relative to the first opening of the formed tubular main liner. At least one jacket is applied about the formed tubular inflation liner. Heat shrink is then applied to cause reflow of the at least one outer jacket forming a fused assembly to the braid, the formed tubular inflation liner to the formed tubular main liner. Thereafter the heat shrink is removed prior to attaching a balloon about the fused assembly. Optionally, prior to the step of positioning the second opening of the formed tubular inflation liner longitudinally relative to the first opening of the formed tubular main liner, the method may further include applying a braid or coil wound about: (i) the formed tubular main liner, not including the formed tubular inflation liner; (ii) the formed tubular main liner and including the formed tubular inflation liner; or (iii) the formed tubular main liner, wherein a part of the braid is wrapped about the formed tubular inflation liner, while another part of the braid is disposed between the formed tubular main liner and the formed tubular inflation liner.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which:

FIG. 1B is a radial cross-sectional view of the balloon catheter of FIG. 1A along dashed line 1B-1B;

FIG. 1C is an enlarged view of the dashed area 1C of FIG. 1A;

FIG. 2A is a schematic view of an alternative configuration of the present inventive balloon guide catheter, while the balloon is in a fully deflated state;

FIG. 2B is a partial longitudinal cross-sectional view of the balloon guide catheter of FIG. 2A;

FIG. 4G is a top longitudinal view of still another configuration of a balloon guide catheter in accordance with the present invention wherein the expandable distal tip is a plurality of fingers and the balloon is secured along a distal weld pattern between the fingers; wherein the balloon is depicted in a deflated state and the expandable distal tip is in a compressed state;

FIG. 4H is the balloon guide catheter of FIG. 4G while the balloon is in an inflated state and the expandable distal tip is in an expanded state;

FIG. 4I is a radial cross-sectional view of the distal end of the catheter of FIG. 4H along lines IV(I)-IV(I);

DETAILED DESCRIPTION OF THE INVENTION

Figure 1A:
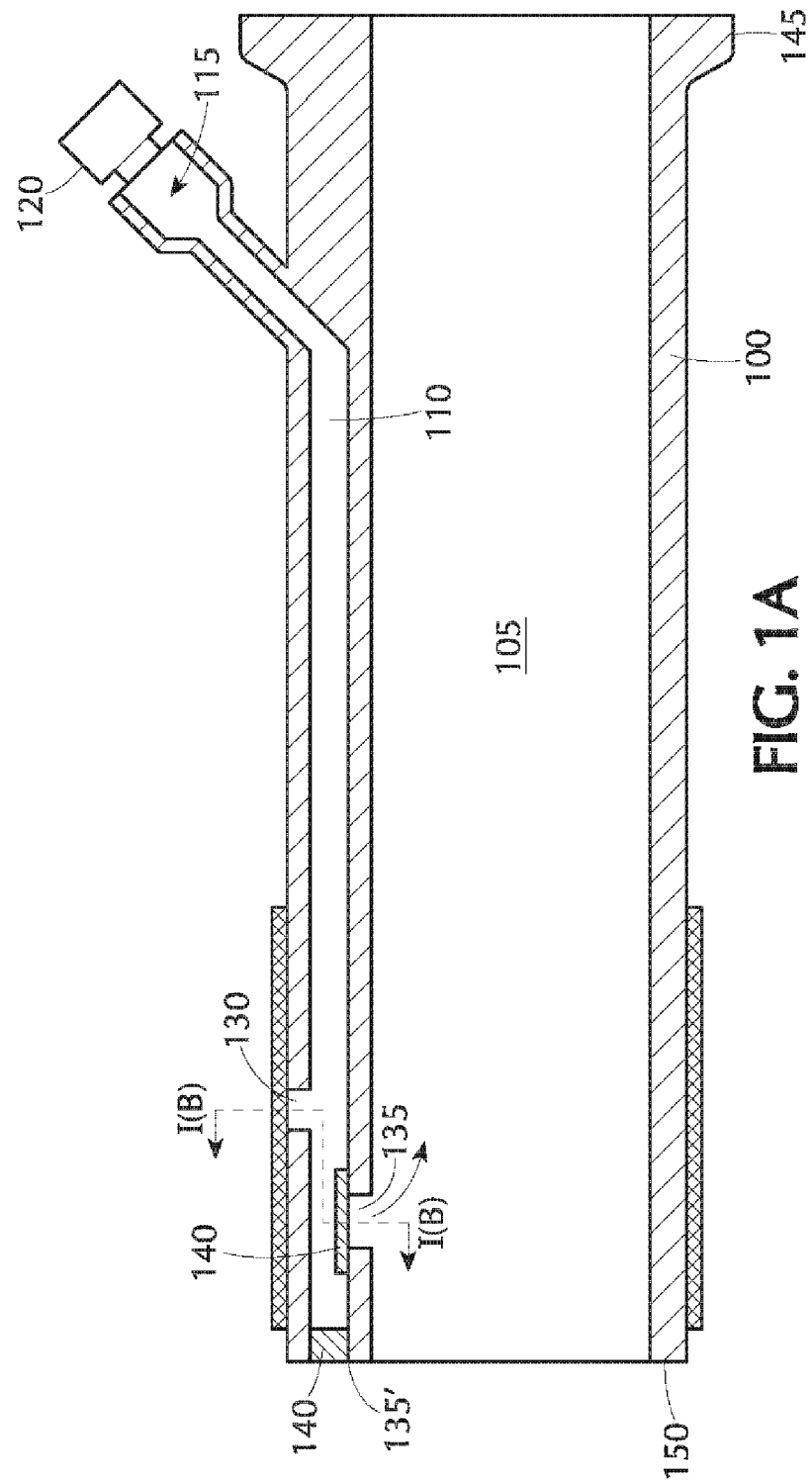
FIG. 1A is a longitudinal cross-sectional view of the present inventive balloon guide catheter with a positive distal venting configuration; the balloon being depicted while in a deflated state.

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionalist. The terms "occlusion", "clot" or "blockage" are used interchangeably.

Conventional balloon catheters have a coaxial design wherein a central lumen disposed centrally of the balloon catheter receives a guidewire therethrough while an inflation lumen is disposed coaxially about and completely/fully encircling the central lumen. The present inventive balloon guide catheter is designed so that the inflation lumen partially-encircles or semi-encircles the main lumen, i.e., the inflation lumen does not completely encircle the inflation lumen. Moreover, the center of the inflation lumen may, but need not necessarily, share the same center as that of the main lumen. FIG. 1G is an alternative configuration of an exemplary radial cross-sectional view of the present inventive catheter illustrating the semi-encircling inflation lumen and main/guide lumen eccentrically arranged (the two lumens not sharing the same center, not concentric), whereas FIG. 1H is another configuration of an exemplary radial cross-sectional view of the present inventive catheter depicting the semi-encircling inflation lumen and main/guide lumen concentrically arranged (the two lumens sharing the same center).

When traversing a tortious path through the vessel of the body, the presently arranged inflation lumen provides improved deliverability by providing a shaft that may be connected throughout the shaft, a connectivity that is not provided with completely/fully encircling concentric (co-axial) conventional designs as concentric designs must be substantially unconnected between outer and inner shafts to provide a concentric lumen. Moreover, the conventional concentric (coaxial) design of the inflation lumen about the central lumen takes up a great deal of valuable cross section area between the inner surface and the outer surface of the catheter, that extends in a substantially uniform manner about the circumference of the catheter when compared to the present inventive partially/semi-encircling design which may have varied wall thickness between the inner surface and the outer surface of the catheter, that varies about the circumference of the catheter and allows for a reduced cross sectional area between the inner surface and the outer surface of the catheter. This variation in wall thickness about the circumference of the catheter allows for a larger inner diameter for a given outer diameter when compared to a conventional fully/completely encircling coaxial design because less material is required to define the inflation/deflation lumen for a given lumen cross sectional area. Ideally, the inner diameter of the present inventive partially/semi-encircling design maintains circularity throughout the catheter shaft to accommodate ancillary devices which mostly maintain circularity longitudinally and the outer surface deviates from circularity to slight ovality in order to accommodate the inflation/deflation lumen. The larger inner diameter for a given outer diameter allows the present inventive catheter to receive ancillary devices with larger outer diameters than would be otherwise accommodated with fully/completely encircling concentric designs with the same given outer diameter. Further, the larger inner diameter of the present inventive design will allow for greater aspiration (co-aspiration with an intermediate catheter) flow rates for a given aspiration vacuum pressure. The greater aspiration flow rate serves to enhance flow reversal within the target treatment location and applies a greater suction force to the face of a clot in the vessel aiding in successful retrieval of the clot with aspiration alone or in conjunction with a stent retriever. It is appreciated that the inner and outer surfaces of the present inventive partially/semi-encircling design may both have ovality. Additional embodiments that maintain outer circularity with inner ovality may also be envisaged. Embodiments with inner ovality will be advantageous in a balloon guide catheter when combined with an inner intermediate catheter having circularity because the extra volume provided between the inner oval cross section of the balloon guide catheter and the outer circular cross section of the intermediate catheter provides additional cross section area between the catheters that can be utilized for aspiration flow. Therefore, when accommodating a given intermediate catheter with outer circularity in balloon guide catheters with a given outer diameter, a balloon guide catheter with an inner ovality will allow for greater aspiration flow rates compared to a balloon guide catheter with an inner circularity, especially so for a concentric design as it will also require a greater cross-sectional area for the wall thickness of the catheter to accommodate the inflation/deflation lumen.

Figure 1D:
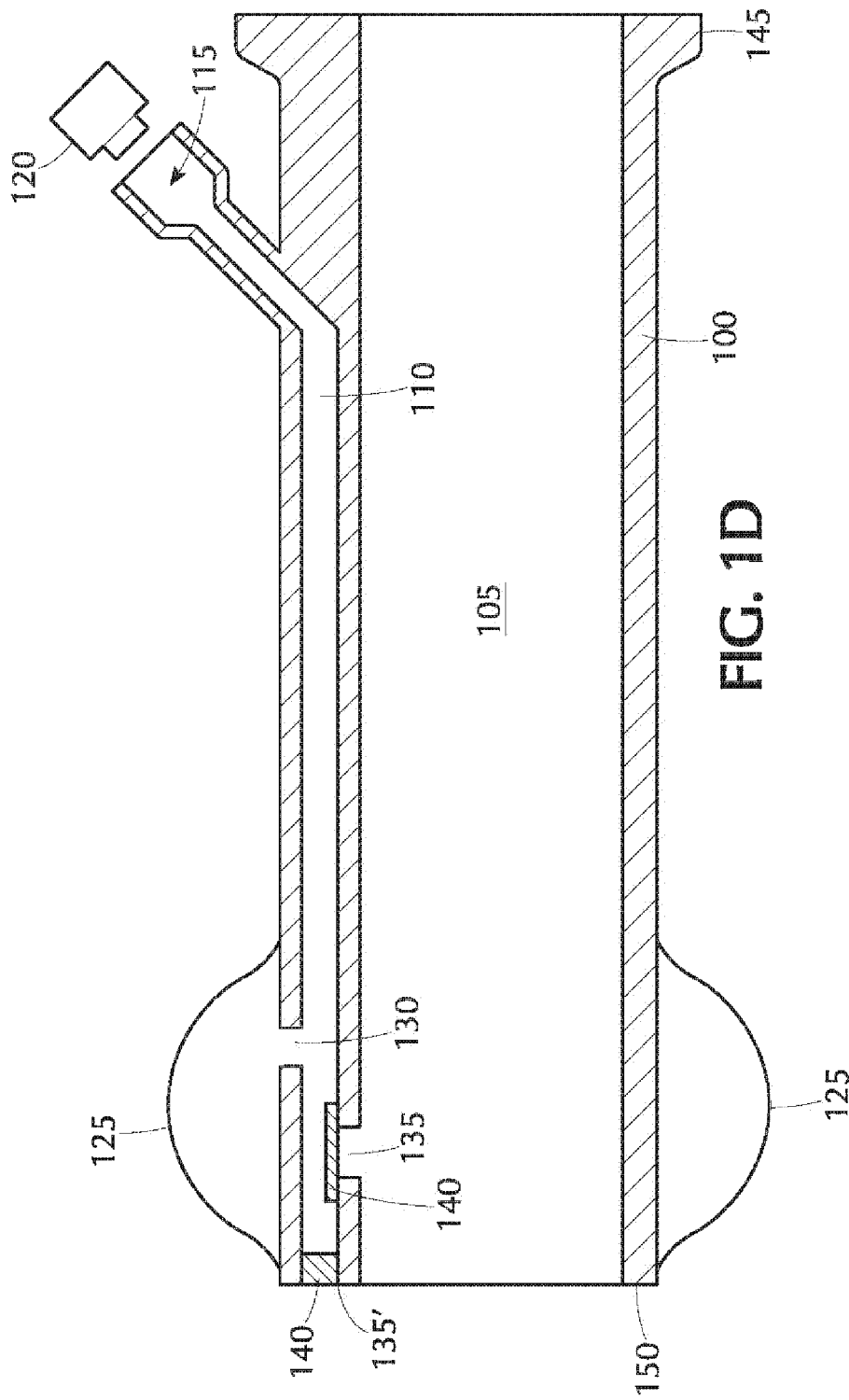
FIG. 1D is a longitudinal cross-sectional view of the present inventive balloon guide catheter of FIG. 1A, with the balloon in a fully inflated state.

Referring to the longitudinal cross-sectional view depicted in FIG. 1A, the present inventive positive venting balloon guide catheter eliminates the need for a vacuum or negative pressure typically required when prepping conventional devices. The inventive balloon guide catheter includes a catheter shaft or body 100 having a main/central lumen 105 defined longitudinally therethrough for receiving a guidewire or other ancillary device. Also defined in the catheter shaft or body 100 is an inflation lumen 110 disposed radially outward from and partially/semi-encircling the main/central lumen 105 (but not sharing a common center), as illustrated in the radial cross-sectional view in FIG. 1B. A proximal end of the inflation lumen is in fluid communication with an inflation port 115. As shown in FIG. 1A, inflation port 115 is typically angled radially outward relative to that of the catheter body 100. A manual device (e.g., a syringe) 120 or an automated pressure device can be attached at a proximal inflation port 115 to generate a positive pressure by dispensing an inflation medium (e.g., liquid) into the inflation lumen 110. The inflation medium is preferably a liquid solution, such as a solution containing water, distilled water, deionized water, heparin, saline, contrast medium/agent or some combination thereof. In a preferred embodiment the inflation medium is a solution of contrast medium and saline, most preferably a solution of a 50:50 ratio of contrast medium to saline. The inflation medium solution is typically stored at room temperature.

The inflation lumen 110 has one or more exhaust vents defined therein. These exhaust vents may be configured to expunge/purge residual air trapped in the inflation lumen in a radial direction, a longitudinal direction or both. In the example shown in FIG. 1A, residual air is purged out from two exhaust vents 135, 135', both disposed towards a distal end 150 of the catheter. One of the exhaust vents 135 is disposed proximally of a distal tip or end 150 of the catheter and defined radially inward in the catheter shaft or body 100 serving as a conduit for fluid communication of the purged residual air between the inflation lumen 110 and the main/central lumen 105. The other exhaust vent 135' is arranged longitudinally at the distal tip or end 150 of the inflation lumen 110. It is contemplated and within the intended scope of the present invention to alternatively have either a radial exhaust vent or a longitudinal exhaust vent, rather than both. Moreover, if the balloon catheter has a radial exhaust vent more than one may be provided, as desired.

A microporous membrane 140 covers each of the exhaust vents 135, 135', wherein the pores of the microporous membrane are sized to permit only the passage of gas (e.g., residual air) therethrough, liquid (inflation medium) dispensed through the inflation lumen is prevented from permeating through the porous membrane allowing the pressure within the inflating lumen to build-up and inflate the balloon as the volume within the balloon fills with the inflation medium. Preferably, the microporous membrane is a certain grade (based on porosity and thickness) of sintered polytetrafluoroethylene (PTFE), for example, sintered polytetrafluoroethylene (ePTFE), that permits the passage of air molecules therethrough but acts as a barrier to larger molecules such as water, saline and contrast medium because of two attributes, (i) hydrophobic membrane and (ii) molar volume. The membrane is hydrophobic in nature and allows the membrane to repel relatively high tension (polar) fluids even with the presence of small pores in a non-pressurized system. Gases on the other hand pass easily through such membranes under very relatively low pressures. For instance, water vapor will pass through the ePTFE microporous membrane, however it is time dependent. With regards to the second factor, the size of the water and contrast medium molecules are greater than the air molecules permitting the air molecule to pass through the membrane containing numerous small pore sizes. In relation to the present invention, the relative sizes of the molecules are the dominant characteristic at play within this application timeframe of injecting fluid through a lumen, where air is expelled through a microporous membrane under relatively high pressure. The micropores of the ePTFE microporous membrane vary in size and are preferably in the size range of approximately 0.02 µm to approximately 500 µm, more preferably in the size range of approximately 5 µm to approximately 100 µm. FIG. 1C is an enlarged view of the dashed area 1C in FIG. 1B that clearly shows the microporous membrane 140 covering the radially disposed exhaust vent 135. In FIGS. 1A-1C the microporous membrane 140 is disposed radially outward of the central lumen 105 (i.e., within the inflation lumen 110). As desired, the microporous membrane may be disposed within the inflation lumen (FIGS. 1A-1C); the microporous membrane may be disposed entirely within the wall between the central and inflation lumens 105, 110, respectively; or a combination thereof in which a first portion of the microporous membrane extends radially inward into the wall between the inflation and central lumens while a second portion of the microporous membrane extends radially outward into the inflation lumen. Preferably, no portion of the microporous membrane extends radially inward into the central lumen since this could potentially result in a snag when passing therethrough an ancillary device.

The inflation lumen 110 extends axially through the catheter body 100 from proximate its proximal end 145 to its opposite distal tip or end 150. An inflation/inlet vent 130 is defined radially outward through the catheter body 100 and serves as a conduit for the inflation medium between the inflation lumen 110 and a balloon 125 covering the inflation vent 130. Balloon 125 is bonded or adhered to an outer surface of a distal portion of the catheter body 100 forming a seal over the inflation vent 130. In the deflated state shown in FIG. 1A, the balloon 125 rests in physical contact against the inflation vent 130 temporarily preventing the passage of the inflation medium therethrough until the built-up pressure in the inflation lumen 110 exceeds a predetermined pressure of the opposing force exerted by the balloon 125.

Figure 1E:
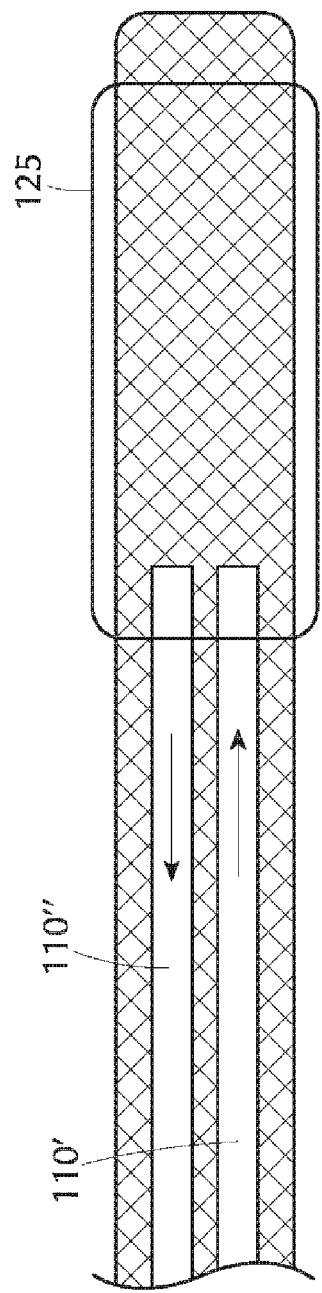
FIG. 1E depicts a partial view of a distal end of an exemplary balloon guide catheter in accordance with the present invention with dual inflation lumen arranged side-by-side.
Figure 1F:
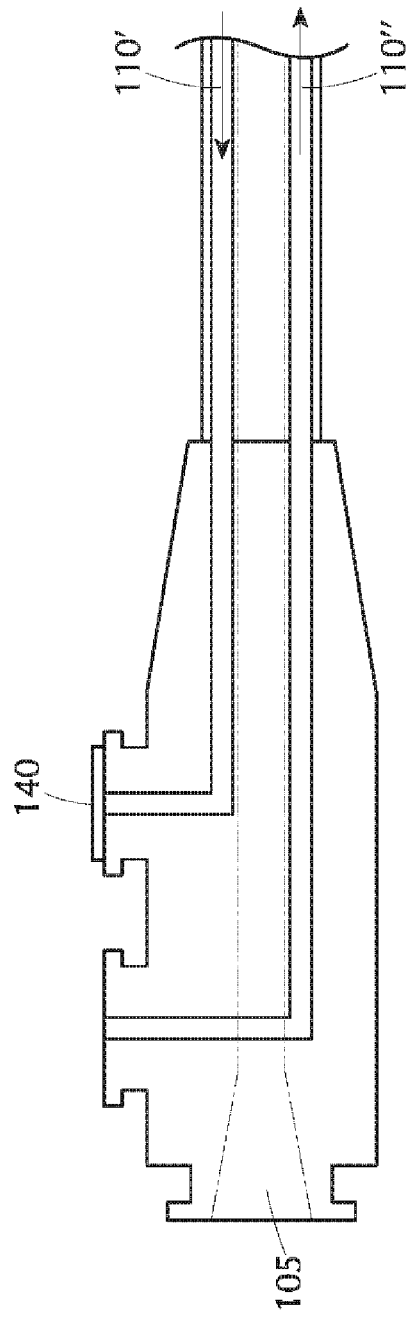
FIG. 1F depicts a partial view of a distal end of another exemplary balloon guide catheter in accordance with the present invention with dual inflation lumen arranged with one inflation lumen disposed above the main/central lumen, while the other inflation lumen is positioned below the main/central lumen.
Figure 5C:
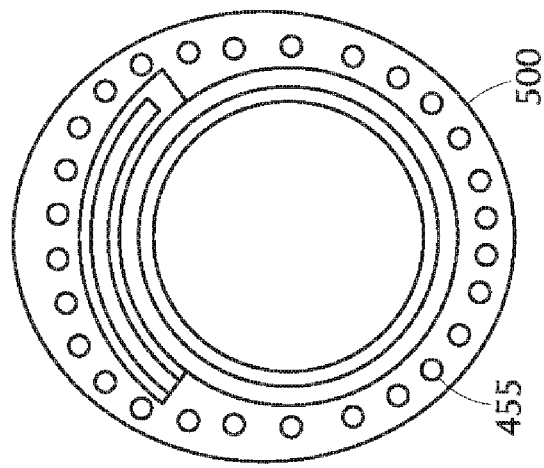
FIG. 5C is a radial cross-sectional view of the catheter of FIG. 5A along lines V(C)-V(C)
Figure 1H:
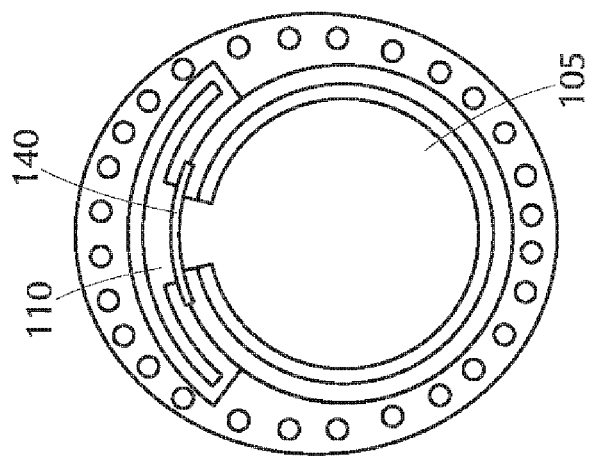
FIG. 1H is another configuration of an exemplary radial cross-sectional view of the present inventive catheter depicting the semi-encircling inflation lumen and main/guide lumen concentrically arranged (the two lumens sharing the same center)
Figure 1G:
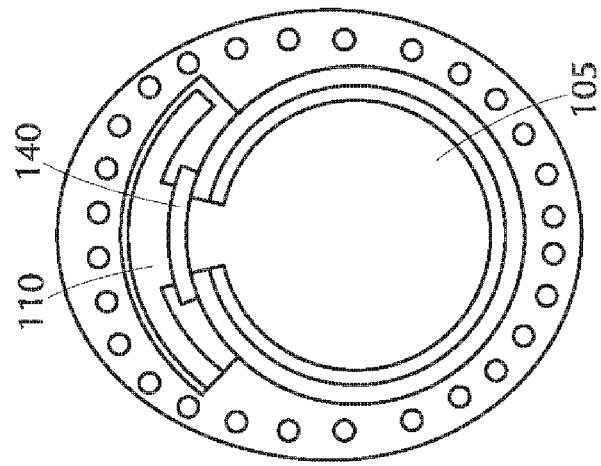
FIG. 1G is an alternative configuration of an exemplary radial cross-sectional view of the present inventive catheter illustrating the semi-encircling inflation lumen and main/guide lumen eccentrically arranged (the two lumens not sharing the same center, not concentric)

The embodiment shown in FIGS. 1A-1C depict the present inventive balloon catheter having a single inflation lumen. It is possible and within the intended scope of the present invention to have more than one inflation lumen. FIG. 1E depicts a dual inflation lumen design 110', 110'' wherein the two inflation lumens are arranged side-by-side. In the first inflation lumen 110', fluid flows through the lumen from the proximal end to the distal end, whereas fluid flows in an opposite direction through the second inflation lumen 110'' from the distal end to the proximal end. Another configuration of the dual inflation lumen design is shown in FIG. 1F. Here the dual inflation lumens are disposed one above and the other below the main/central lumen. That is, a first inflation lumen 110' is arranged above the main/central lumen 105, while the second inflation lumen 110'' is disposed below the main/central lumen 105. The first inflation lumen 110' having fluid flowing therethrough from the distal end to the proximal end has a microporous membrane 140 at the port so that residual gas is able to pass, but inflation medium is prohibited from passage through the membrane causing the balloon to inflate when the residual air has been purged, expelled or flushed from the system.

Figure 2C:
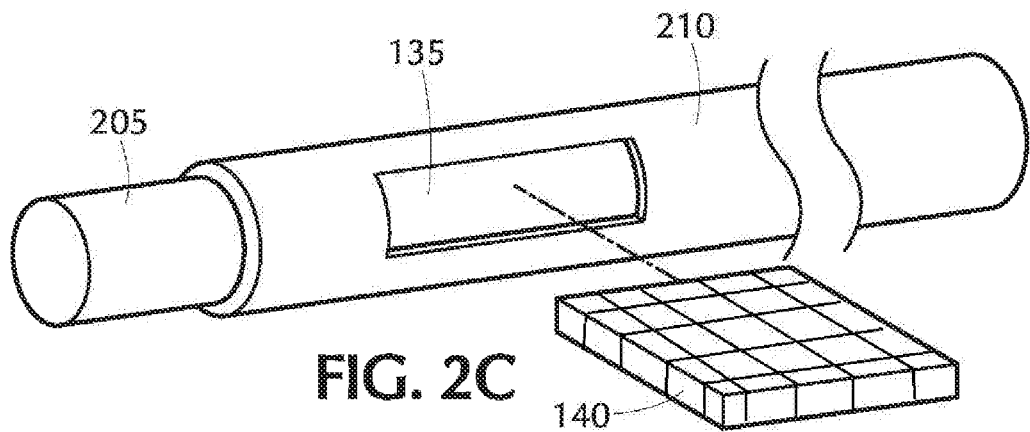
FIGS. 2C-2G depict a series of sequential stages or steps during the manufacture of the balloon guide catheter of FIG. 2A.
Figure 2D:
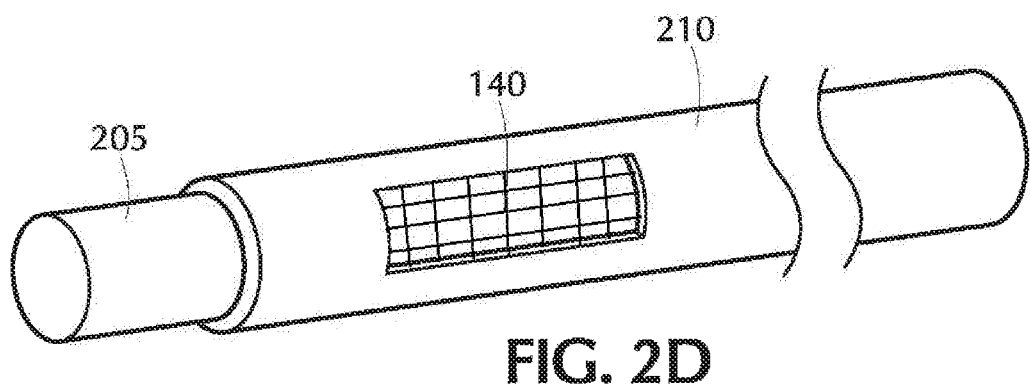

Perspective and longitudinal cross-sectional views of the assembled catheter in accordance with the present invention are depicted in FIGS. 2A & 2B, respectively. While FIGS. 2C-2G depict a series of sequential steps or stages during assembly and manufacture of the catheter shown in FIGS. 2A & 2B. Initially, in FIG. 2C, the main/central lumen 105 may be formed by wrapping a main/central liner 210 (e.g., made of PTFE) about a mandrel 205 to produce a formed main/central tube. Preferably, the mandrel 215 is a Silver Plated Coated (SPC) mandrel dipped with a PTFE layer (typically, approximately 0.00075"-approximately 0.001")

in wall thickness and is thereafter etched. A polymeric strike layer (e.g., a polyether block amide (PEBAX®) or urethane material) is coated over the etched PTFE. The wall thickness of the polymeric strike layer may be a few thousandths of an inch, but for this application a thickness of approximately 0.00025" would be sufficient to communicate and adhere with the reflowing polymer jacket materials, as described in detail below. Alternatively, a preformed tube may be used as the main/central tube. A first hole or opening is radially punched through the formed tubular main/central inner liner 210 (PTFE on the SPC mandrel) that serves as the radial exhaust vent 135 into the main/central lumen 105. A selected grade (based on desired porosity & thickness) of sintered PTFE forming the microporous membrane 140 is cut either from a patch or from a tubular configuration for easier mounting and locating around the mandrel 205 and formed tubular main/central inner liner 210. Selected sections of or the entire surface of the microporous membrane 140 on both sides may be treated (e., etched using conventional techniques) to promote the application of a thin polymeric strike layer at selected sections or edges of the microporous membrane 140, the microporous membrane forming an intrinsic weld with the catheter polymeric substrates along the polymeric strike layer Like the microporous membrane, the formed tubular PTFE main/central inner liner 210 is also treated (e.g., etched) and is prepped with a polymeric strike layer. Referring to FIG. 2D, the cut microporous membrane 140 is positioned, preferably centered, over the punched exhaust vent 135 defined in the formed tubular PTFE main/central inner liner 210. Thereafter, the formed tubular PTFE main/central inner liner 210 is attached (e.g., welded or bonded) together with the cut microporous membrane 140 under the application of heat during the laminating construction processing steps of the catheter.

Figure 2E:
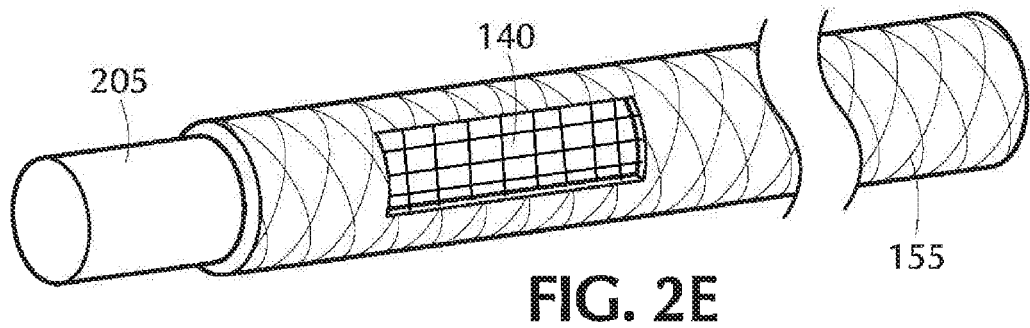
Figure 2F:
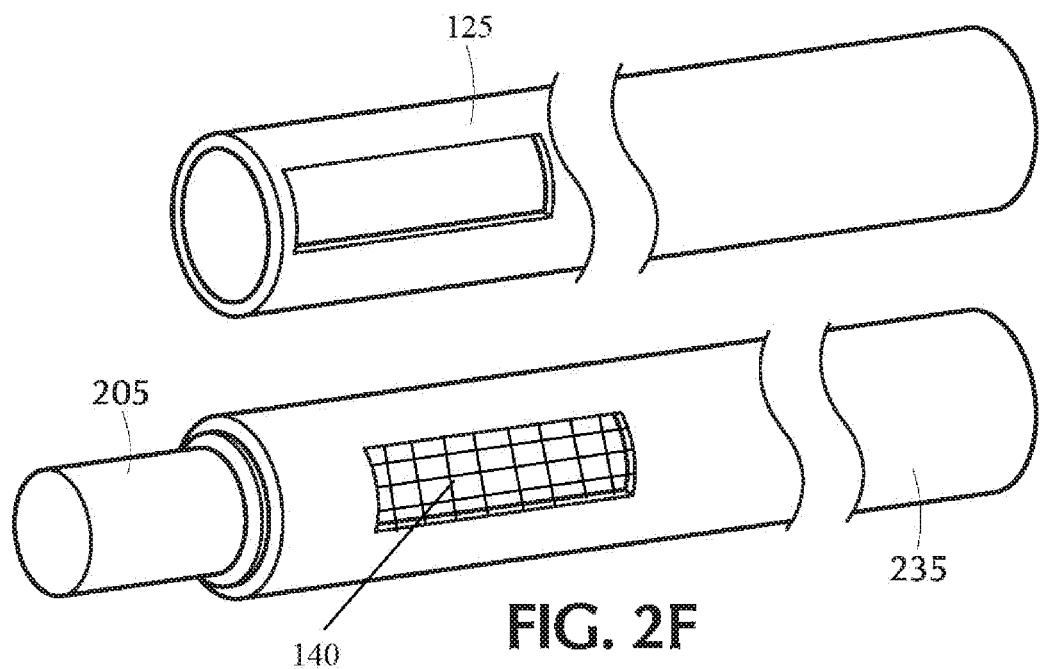

As shown in FIG. 2E, using a wire braiding machine, a braid or a coil 155 is tightly applied or wound about the assembled SPC dipped mandrel 205 with the formed tubular ePTFE main/central liner 210 and ePTFE microporous membrane patch 140. Braid 155 provides both structural support as well as retaining the ePTFE microporous membrane patch 140 to the tubular formed ePTFE main/central liner 210. Thereafter, a polymer jacket material 235 with a skived port is located directly over the skive. In FIG. 2F, heat shrink tubing is positioned over the assembly, then heat is applied to get the materials to reflow and bond together, thereafter the heat shrink tubing is removed. Preferably, fluorinated ethylene propylene (FEP) heat shrink is slid over the assembly and heat is applied to cause reflow of the polymer jacket material 235 to bond to the braid, etch/strike portion of the membrane as well as to the strike layer covering the PTFE.

Figure 2G:
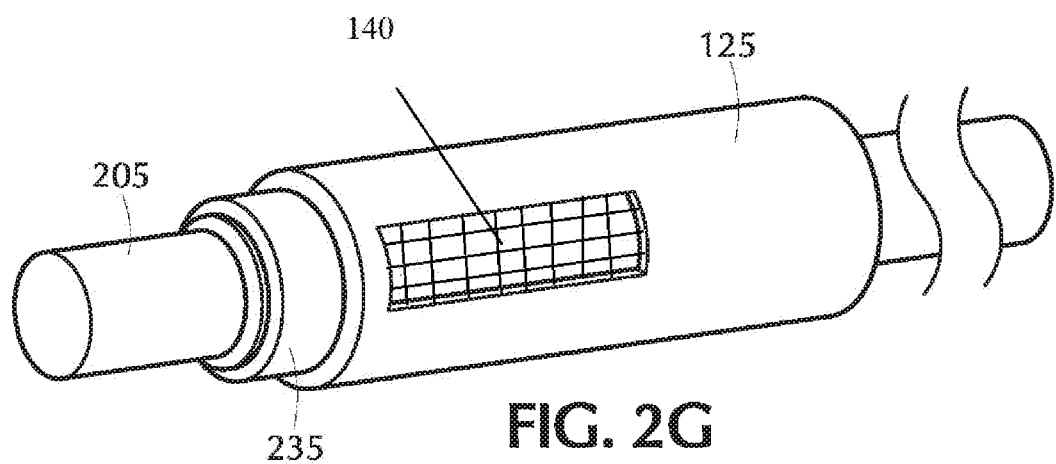
Figure 5A:
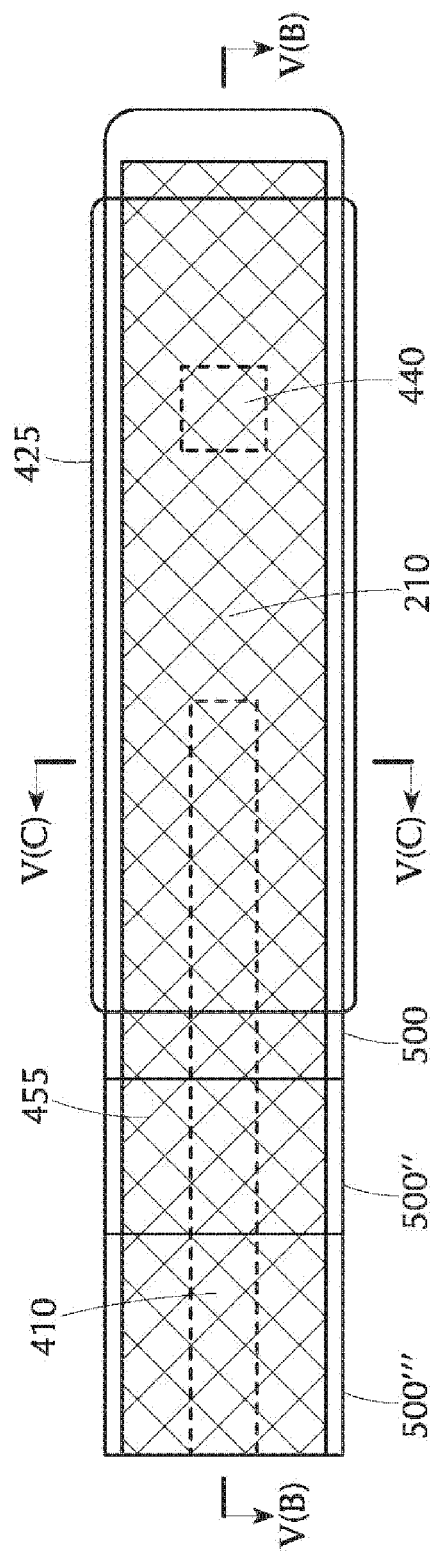
FIG. 5A is a top longitudinal view of the assembled balloon guide catheter illustrating the exemplary braid configuration in which one part of the braid is depicted radially outward of the inflation liner and another part of the braid is depicted radially inward of the inflation liner; as well as depicting the optional three separate polymer jackets disposed about each of the central liner, braid and inner liner.
Figure 5B:
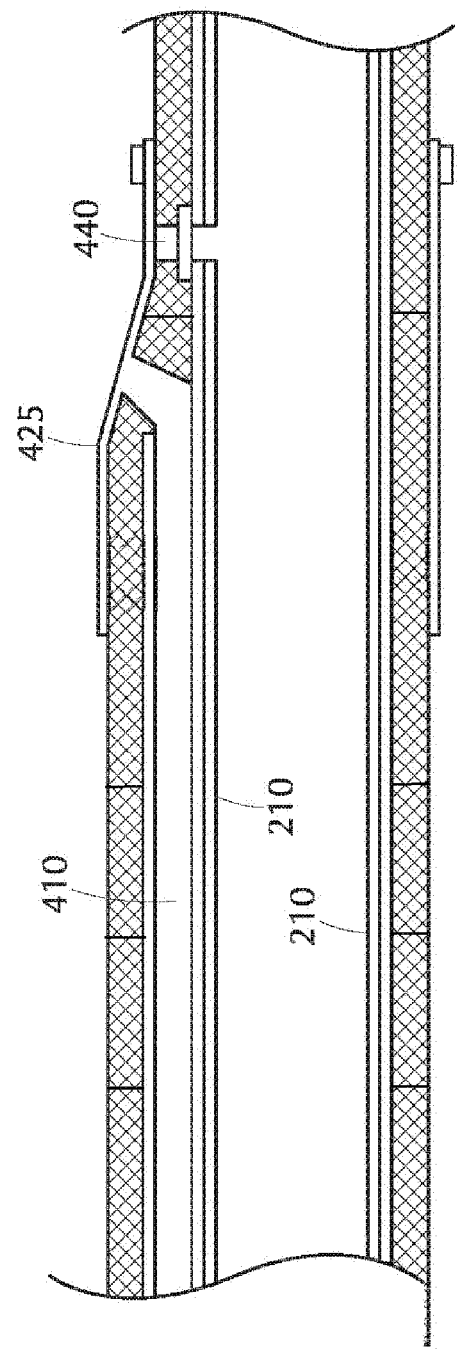
FIG. 5B is longitudinal cross-sectional view of the catheter of FIG. 5A along lines V(B)-V(B)

A separately formed inflation liner 410 (e.g., PTFE) is wrapped about its own internal mandrel (e.g., SPC mandrel) forms the inflation lumen 110, as shown in FIG. 5A. The formed tubular inflation liner may be positioned above the braid, below the braid or between the braid strands (i.e., part of the braid is above the formed tubular inflation liner, while another part of the braid is below the formed tubular inflation liner). Alternatively, a preformed tube may be used as the formed tubular inflation liner. The formed tubular ePTFE inflation liner may be positioned longitudinally relative to the formed tubular main/central liner. In one configuration the formed tubular inflation liner and main/central liner are arranged such that the ePTFE microporous membrane 140 and the exhaust vent 130 to the balloon 125 are substantially radially aligned with the radial exhaust vent 135 (as shown in FIGS. 2A & 2B). Alternatively, as illustrated in FIG. 1A, the microporous membrane 140 and inflation vent 130, need not be radially aligned with the radial exhaust vent 135. The assembled outer jackets, braid, inflation lumen and liner are fused together during reflow when subject to FEP heat shrink processing. Prior to attachment of the balloon the FEP heat shrink is removed. The balloon 125 in FIG. 2G is positioned over the fused assembly of the outer jackets, braid, inflation lumen and liner so that the balloon covers the inlet vent 130. Then the balloon is heat welded at both ends to create an intrinsic weld with the outer surface of the catheter shaft or body 100.

Referring to FIG. 5A several additional thermoplastic outer tubes, sleeves or jackets (500, 500', 500") with varying shore hardness may be positioned over the respective main/central liner 210, braid 455, and inflation liner 410 to tailor the finished catheters stiffness profile as desired. The jackets are placed one after another to vary the stiffness of the catheter along its length. Jackets of different hardness are arranged over the central lumen, braid and inflation lumen assembly, each jacket disposed longitudinally serially one butted up against (in physical contact with) the next jacket, or a space may be left for material to flow into between adjacent jackets. The longitudinally disposed singular outer jackets allow for a lower profile wall thickness which is a function of how low a wall thickness that can be extruded for a particular material. These jackets are reflowed through the braid pattern and bond with the strike layers of the central and inflation lumens. The reflow process includes threading a FEP heat shrink tube over the assembly, applying heat to reflow the jackets, and removing the FEP heat shrink afterwards. The balloon is then heat welded to the assembly. Radially disposed outer jackets are possible.

Once the components have been assembled and positioned as desired, an insert is preferably placed to prevent sealing of the opening during heating and thereby maintain fluid communication in the following areas: (i) at the end of the inflation lumen; (ii) between the balloon and the inflation lumen; (iii) as well as between the inflation lumen and the PTFE microporous membrane. Heat is applied whereby the thermoplastic materials reflow to form a secure assembly while the insert prohibits sealing of the communication channels. Lastly, the insert is removed and the balloon 125 is assembled (e.g., heat welded) to the secure assembly. In the configuration in FIGS. 2A & 2B, a distal end of the balloon 125 is sealed within the wall of the catheter (i.e., between the PTFE central liner and the outer jacket). Thereafter, the balloon 125 is inverted and its proximal end is laser welded to the outer surface of the assembled catheter body. In an alternative configuration depicted in FIG. 1A, rather than wrap around the distal end or tip 150, the balloon is laser welded to the outer surface of the catheter shaft at both its proximal and distal ends. A luer or other connector 160 may be attached to the proximal end of the assembled catheter.

The location of the inflation/exhaust vents encourages full venting of the residual air and only when the residual air has been fully bled, will the balloon inflate with the inflation medium initially used to bleed the catheter of residual air. To facilitate this, the inflation port size and exhaust vent size is preferably optimized so that the pressure required to inflate the balloon is greater than the pressure required to vent residual air.

In FIGS. 2A-2G, braid 155 is wound about the outer perimeter of the assembled formed tubular PTFE main/central liner and ePTFE microporous membrane secured thereto to retain the microporous membrane in position. The ePTFE microporous membrane may otherwise be positioned over the braid, that is, the braid wrapped about the outer perimeter of the formed tubular main/central liner entirely radially inward (i.e., under/beneath) of the formed tubular inflation liner. While in another design the braid may be wrapped about the outer perimeter of the assembled formed tubular PTFE main/central liner, ePTFE microporous membrane and formed tubular inflation liner. In still yet another configuration, one part of the braid may be wound radially inward (i.e., under/beneath) the formed tubular inflation liner (i.e., between the formed tubular inflation liner and the formed tubular main/central liner) and another part radially outward (i.e., over/above) the formed tubular inflation liner (as shown in FIG. 5A).

The present inventive balloon guide catheter with positive venting is prepped by a physician or interventionalist prior to introduction into the body. Specifically, a syringe 120 containing an inflation medium is connected to the inflation lumen 110 via the inflation port 115. As the physician or interventionalist dispenses the inflation medium into the inflation lumen 110 using the syringe 120 the residual air therein is pushed by the inflation medium through the inflation lumen 110 in a distal direction. Since the residual air is positively pushed through the inflation lumen by the inflation medium the need for a vacuum or negative pressure to purge the residual air from the catheter is eliminated. In greater detail, initially, when the balloon is deflated and tightly wrapped in physical contact against the outer surface of the catheter body, the residual air follows the route or path of least resistance passing through the microporous membrane 140 and exiting from the catheter body through the exhaust openings 135, 135'. As the inflation medium is introduced into the inflation port, only the residual gas (e.g., air) permeates through the microporous membranes 140 and outward through the respective radially and longitudinally configured exhaust openings 135, 135'. Since the microporous membranes 140 prohibit the liquid inflation medium from permeating therethrough, initially due to the fact that the residual gas (e.g., air) previously trapped inside the catheter passes through the porous membranes and outward from the exhaust openings 135, 135' the pressure in the inflation lumen 110 remains somewhat equalized or constant. However, once the residual gas (e.g., air) in the catheter has been bled, continued dispensing of the pressurized inflation medium into the inflation lumen causes a build-up of pressure at the inflation opening 130 exerting a radially outward force on the balloon 125 causing it to expand radially outward as it fills with the inflation medium. FIG. 1A depicts balloon 125 while in a deflated state; whereas FIG. 1D depicts the balloon while in a fully inflated state, once the residual air has been purged from the catheter and the inflation medium has completely filled the balloon.

Only one inflation opening 130 is shown in FIG. 1A, but more than one inflation opening is contemplated and within the intended scope of the present invention for faster inflation/expansion of the balloon 125. While in a deflated state (as seen in FIG. 1A), balloon 125 is in physical contact with the outer surface of the catheter body sealing the inflation opening 130 closed so that the flushing medium is unable to pass therethrough until the pressure exerted on the balloon at the inflation opening 130 exceeds a predetermined threshold.

Figure 3A:
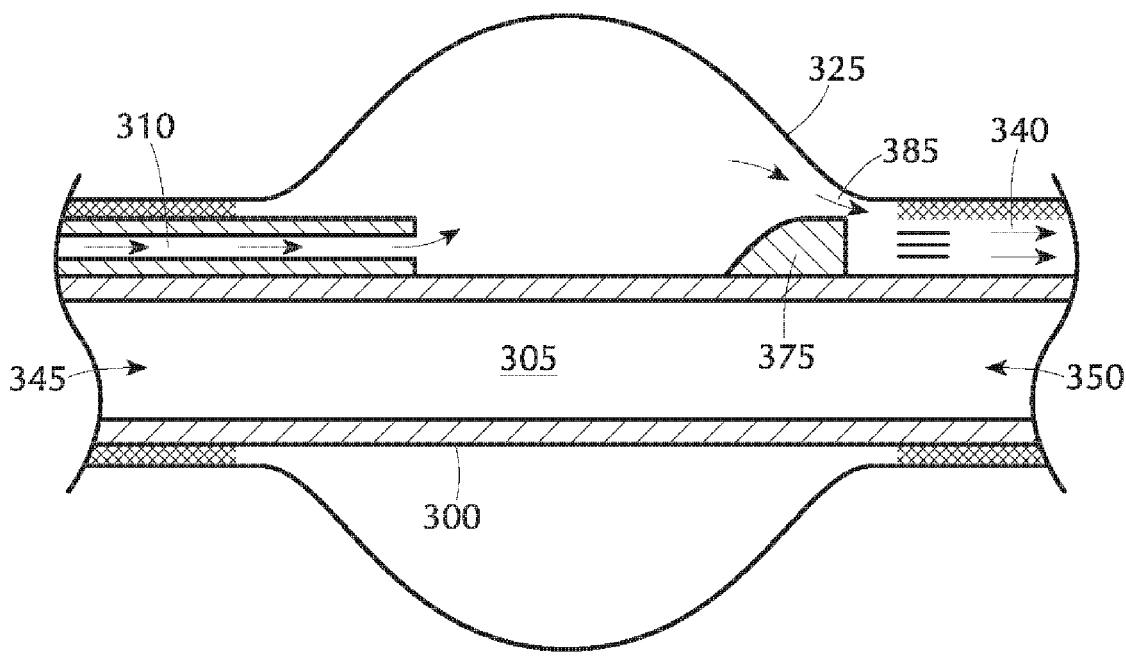
FIG. 3A is a partial longitudinal cross-sectional view of a sealing bump feature of the present inventive positive venting balloon guide catheter; wherein when the balloon is in an inflated state residual gas is permitted to escape via a longitudinally disposed exhaust vent at the terminating end of the inflation lumen and through a porous membrane.
Figure 3B:
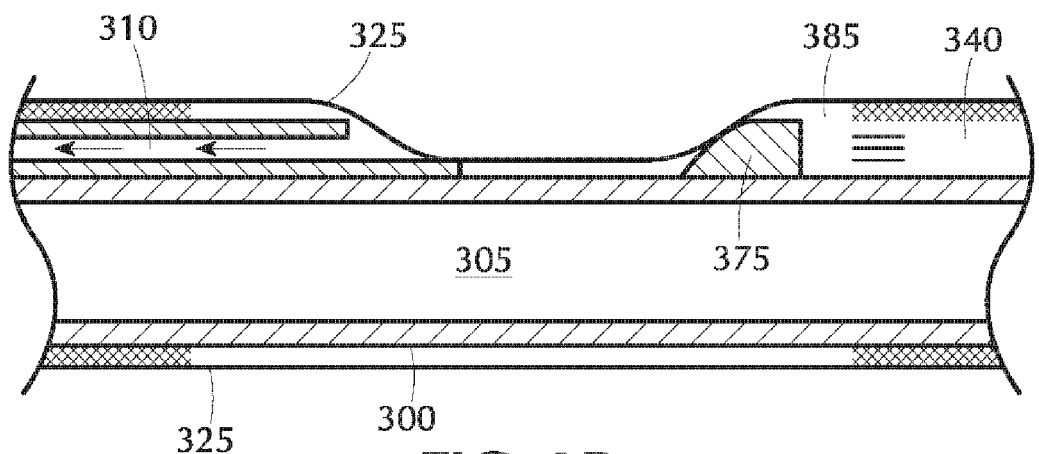
FIG. 3B is partial longitudinal cross-sectional view of the balloon guide catheter of FIG. 3A with the balloon in a deflated state sealed against the bump to prohibit passage of residual air proximally through the exhaust vent.

An alternative configuration of the main/central lumen 305 and partially/semi-encircling inflation lumen 310 of the present inventive balloon guide catheter is shown in FIG. 3A, wherein the balloon is in an inflated state. Once again inflation medium is received in the proximal end 345 and purged or expelled from the distal end 350. Balloon 325 is laser welded at its proximal end directly to the catheter shaft or body 300, while at its opposite distal end of the balloon 325 distal pores 340 (e.g., a microporous membrane or a plurality of longitudinal openings) are disposed at the interface between the balloon and outer surface of the catheter body. Microporous membrane 340 is similar to that described in detail with respect to the previous embodiments and allows only the passage of a residual gas (e.g., residual air) therethrough, prohibiting passage of any liquid/solution (e.g., inflation medium). A bump, projection, protrusion or other raised surface 375 extends radially outward from the outer surface of the catheter body and is located proximally of the microporous membrane 340. During prepping of the balloon guide catheter prior to insertion into the blood vessel, the device is positioned with the distal end pointing upwards. When inflation medium is injected through the inflation lumen, residual gas is directed over the bump 375 with a slight expansion in the balloon 325 and exits through the microporous membrane 340. Once the air has escaped, the passage of inflation medium is blocked by the microporous membrane 340 and the balloon 325 fully inflates with increasing pressure. However, the physician or interventionalist need only partially inflate the balloon 325 until there is no residual gas visible within the balloon. Prior to insertion into the body, inflation medium is retracted back into the syringe under negative pressure/vacuum and the balloon 325 deflates. The balloon 325 while in a deflated state forms a seal against the bump, projection or protrusion 375 preventing the passage of gas in a proximal direction back into the balloon, thereby maintaining the lumen purged of air in a deflated state prior to insertion into the body.

In yet a further modification of the configuration of the balloon catheter in accordance with the present invention, the assembled catheter body at its distal end may be configured to have an expandable distal end or tip 450 as depicted in FIGS. 4A-4D. The expandable distal end or tip being in an expanded state having a larger diameter when the balloon is inflated, relative to the smaller diameter of the expandable distal end or tip of the catheter while in a compressed state when the balloon is deflated. Specifically, the expandable distal end or tip 450 is divided into a plurality of separable expandable fingers 480 radially compressible together by an over molded balloon 425. In this particular configuration, rather than substantially conform to the outer contour of the expandable fingers, while in an inflated state the over molded balloon instead is pulled taught across and is in physical contact only with the tips or ends of the fingers (no physical contact of the balloon between the fingers). In the configuration shown in FIGS. 4A & 4B, the balloon is only welded or secured about the outer perimeter of the catheter shaft distally of the porous membrane 440 coinciding with punch hole through main liner 210 and outer jacket 500. Other methods of attachment are contemplated and within the intended scope of the present invention for securing the balloon around the expandable separable fingers such as adhesive bonding or thermal fusion, as described in detail further. The expandable distal end or tip 450 of the catheter may be divided into any number of two or more expandable separable fingers 480, as desired. The more fingers 480, the shorter the distance that the expandable material between adjacent separable fingers needs to spread apart from one another when the balloon of the catheter is inflated with the inflation medium. The less fingers 480, the larger the diameter that the fingers will expand to. The space between fingers can be adjusted, as desired. That is, the space between adjacent fingers may be increased to allow for sufficient expandable material such that the force to expand the material is relatively low; the space between adjacent fingers may be reduced such that the expandable material reaches maximum expansion at a predetermined diameter. The fingers may optionally include features that aid in minimizing lateral bending forces to optimize flexibility when navigating through tortuous paths.

Figure 4A:
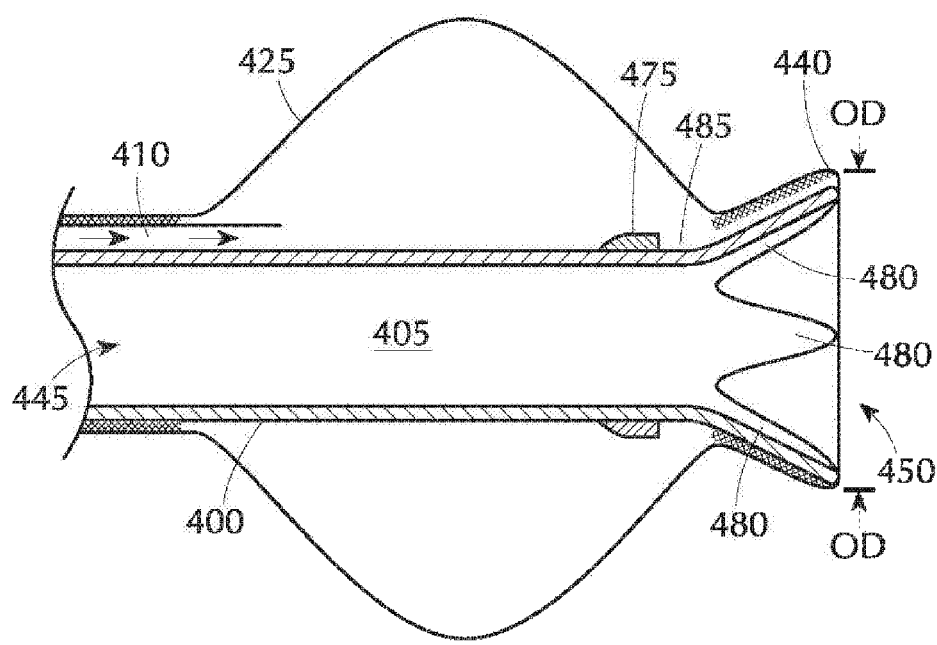
FIG. 4A is a partial longitudinal cross-sectional view of yet another configuration of a balloon guide catheter in accordance with the present invention having an expandable distal tip comprising a plurality of expandable separable fingers; wherein the balloon is depicted in an inflated state and the expandable distal tip is in an expanded state.
Figure 4B:
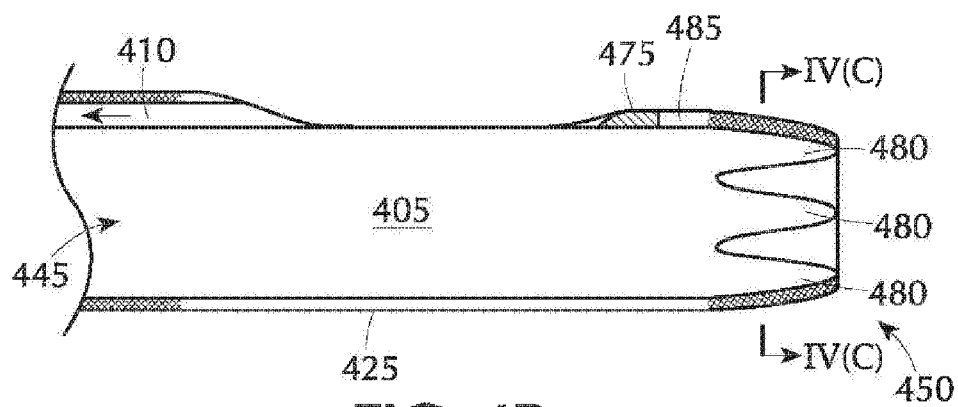
FIG. 4B is a partial longitudinal cross-sectional view of the balloon guide catheter of FIG. 4A with the balloon in a deflated state and the expandable distal tip in a compressed state.

Prior to dispensing the inflation medium into the inflation lumen 410, the balloon 425 is in a deflated state and the expandable distal end or tip 450 of the catheter is in a radially compressed state, as seen in FIG. 4B. While in this radially compressed state, adjacent fingers 480 have the smallest distance separation therebetween such that the outer diameter of the distal end or tip is less than or equal to the outer diameter of the remaining portion of the catheter. While the balloon 425 is in a deflated state it is pulled taught in physical contact against the bump 475 serving as a deflating seal to prohibit passage of residual gas (e.g., air) through the exhaust vent 485 in a proximal direction back into the balloon 425.

Referring to FIG. 4A, during inflation, balloon 425 expands radially and contracts longitudinally thereby with it pulling the expandable distal tip 450 proximally and enlarging the distance separation between adjacent fingers 480. With such enlarged distal end or tip a wider mouth is provided on the distal end of the catheter for aspiration and affording greater aspiration force when engaged with a clot. Once the clot is engaged, aspiration force may be maintained while the balloon is deflated and the distal mouth compresses the clot radially to assist in gripping the clot for extraction through a larger guide or balloon guide catheter. The balloon may vary in thickness, as desired, in defining the specific expansion profile of the balloon and expandable distal end or tip 450.

Figure 4C:
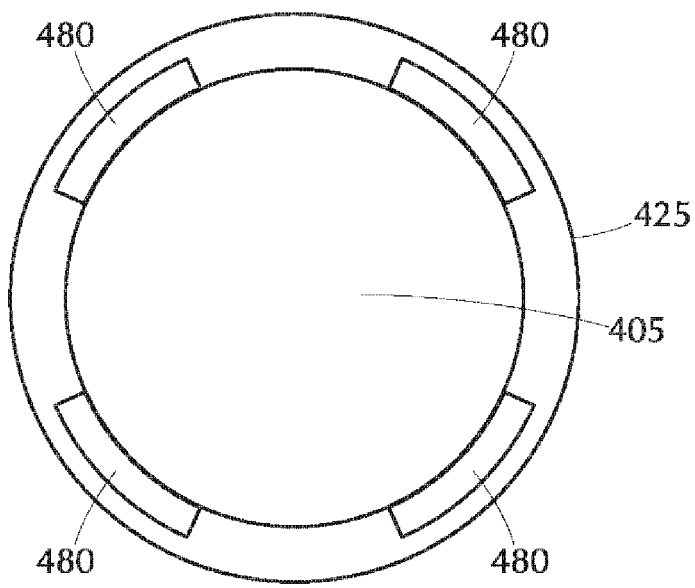
FIG. 4C is a radial cross-sectional view of the expandable distal tip of the catheter of FIG. 4B along lines IV(C)-IV(C)
Figure 4D:
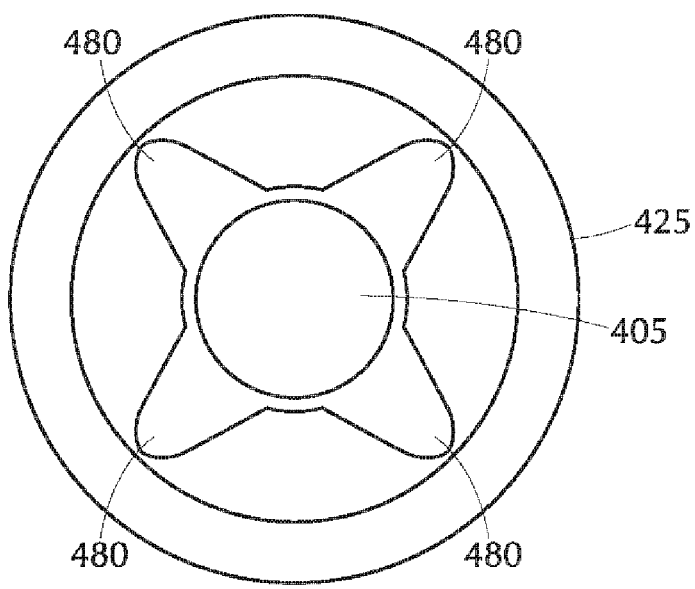
FIG. 4D is an end view of the expandable distal tip of FIG. 4A.

FIG. 4C is a radial cross-sectional view of the four fingers of the catheter in FIG. 4B along lines IV(C)-IV(C), while the fingers are in a compressed state (reduced diameter) and the balloon is deflated. Another view, in FIG. 4D, depicts an end view of the expandable distal tip in FIG. 4A and, in particular, the four fingers of the expandable distal end or tip in an expanded state (enlarged diameter) with the balloon inflated.

Figure 4E:
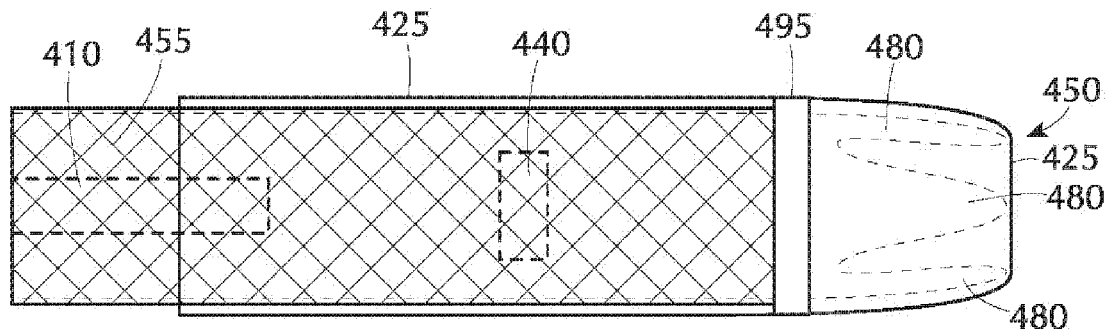
FIG. 4E is a top longitudinal view of another configuration of a balloon guide catheter in accordance with the present invention wherein the balloon encapsulating the expandable distal tip is radially restrained by a restriction band; wherein the balloon is shown in a deflated state and the expandable distal tip is in a compressed state.
Figure 4F:
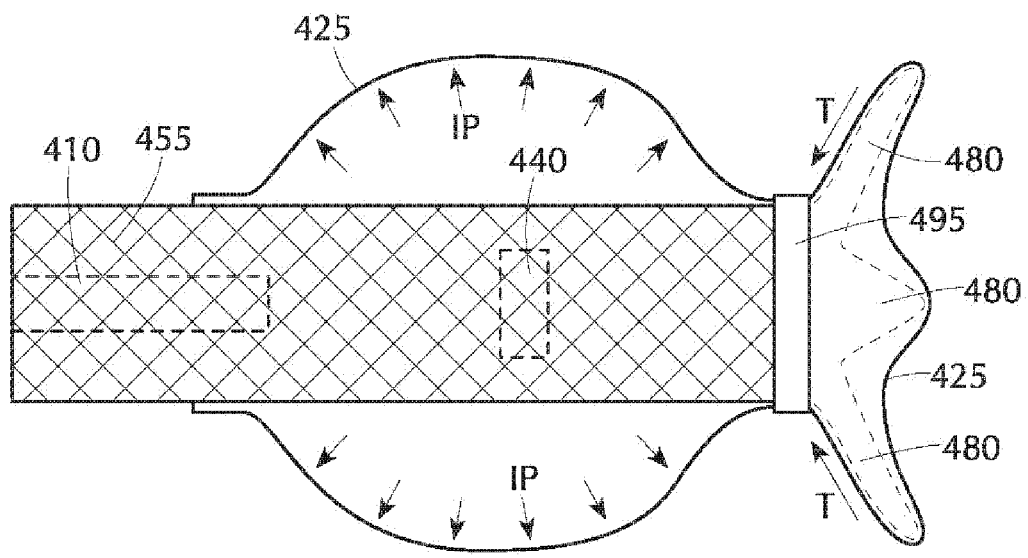
FIG. 4F is the balloon guide catheter of FIG. 4E while the balloon is shown in an inflated state and the expandable distal tip is in an expanded state.

A restrictive band 495 may be disposed about the balloon proximally of the expandable distal end or tip 450 (FIG. 4E) to restrict radially the diameter of the balloon when inflated, as shown in FIG. 4F. If a radiopaque material is selected for the restrictive band 495, the band may serve the dual function of a marker during navigation of the catheter to a target site in a vessel. Balloon 425 is adhered or secured proximally to the outer surface of the catheter shaft, distally encapsulating the fingers 480 without being secured in any manner (uncoupled) beneath the restrictive band 495. Accordingly, during inflation/deflation of the balloon 425 with inflation medium any sliding movement of the balloon 425 beneath the restrictive band 495 is unhindered and permitted. As the balloon 425 is inflated with inflation medium the pressure within the balloon increases (as denoted by the "IP" arrows) causing the balloon to enlarge in diameter, in turn, applying tension (as denoted by the "T" arrows) to the balloon material causing the fingers to open or separate thereby increasing in diameter the expandable distal tip. Preferably, the expandable distal tip or end 450 expands to an outer diameter greater than the outer diameter of the inflated balloon.

Yet another alternative configuration of the expandable distal tip or end of the catheter is illustrated in FIGS. 4G & 4H. In this particular design a proximal end of the balloon is secured to the outer surface of the catheter shaft proximate while the opposite end of the balloon is distally secured (e.g., bonded or welded) between the fingers. Such distal weld pattern (as denoted by the dashed lines) advantageously seals the balloon and promotes expansion of the fingers during inflation, as shown in FIG. 4H as well as the distal end view in FIG. 4I of distal expandable tip in FIG. 4H.

Figure 6A:
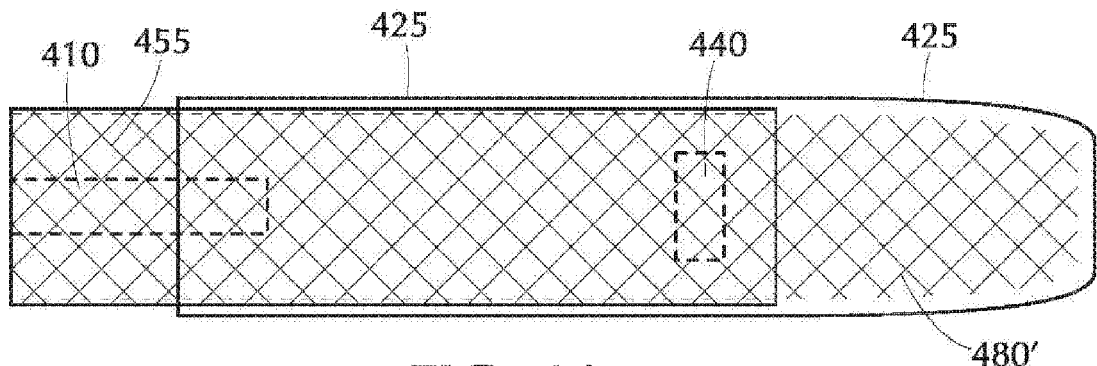
FIG. 6A is a top longitudinal view of an alternative expandable distal tip of an assembled balloon guide catheter in accordance with the present invention; wherein the expandable distal tip is an expandable mesh or braid; the expandable distal tip is depicted in a compressed state with the balloon deflated.
Figure 6B:
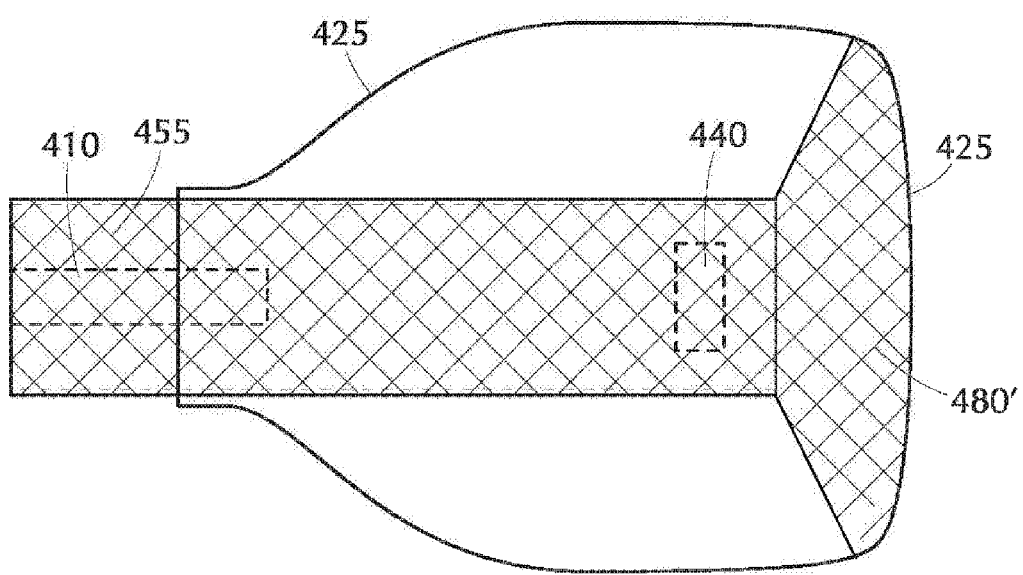
FIG. 6B is a top longitudinal view of the catheter of FIG. 6A with the expandable distal tip depicted in an expanded state with the balloon inflated.

A last configuration of the expandable distal end or tip of the catheter is depicted in FIGS. 6A & 6B, wherein the fingers are replaced with an expandable cage, mesh or braid 480' attached to a distal end of the catheter shaft. The proximal end of the balloon 425 is secured to the outer surface of the catheter shaft while its opposite distal end encapsulates the braid 480' and is coupled distally to the distal end of the main shaft via the braid. By selecting a particular braid pattern and the desired degree of expandability of the expandable balloon material over the expandable distal tip, the braid 480' is pulled open (i.e., increases in diameter) as the balloon inflates/expands with inflation medium. It is noted that no portion of the formed tubular PTFE main/central liner is present at (i.e., not extend distally into) that portion of the distal end or tip of the catheter which is intended to expand (e.g., fingers 480 or braid 480') as this would restrict the distal end or tip from expansion, however, the distal terminating end of the formed tubular PTFE main/central liner may extend axially to and hence reinforce a location at which the expandable distal end or tip is hingedly connected to the distal end of the catheter shaft. Furthermore, the distal end of the balloon may be inverted at the distal tip of the catheter where it extends proximally to encapsulate the braid.

In each of the inventive embodiments described herein, since residual air is exhausted distally from the catheter, the present inventive balloon catheter is to be prepped by purging the device prior to being introduced into the body. Failure to purge the catheter prior to introduction into the body will result in the exhausted residual air undesirably entering the vascular system potentially causing harm to the patient. The positive venting system associated with the present inventive balloon guide catheters simplifies the prepping steps for purging residual air from the device thereby minimizing barriers to use of the device by physicians or interventionalists.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A balloon guide catheter comprising:
a catheter shaft having an outer surface, a proximal end, and an opposite distal end; the catheter shaft having an inner surface forming a main lumen defined therein extending axially therethrough from the proximal end to the distal end; the main lumen being configured to receive a guidewire therein; the catheter shaft between the inner and outer surfaces having an arc shape inflation lumen defined axially therein arranged semi-encircling the main lumen; the catheter shaft having an inlet vent defined in the outer surface radially outward from the inner surface of the catheter shaft and in fluid communication with the inflation lumen; and the catheter shaft having a first exhaust vent disposed longitudinally through a distal terminating end of the inflation lumen coinciding with a distal terminating end of the main lumen;
a first porous membrane disposed at the first exhaust vent within the distal terminating end of the inflation lumen; the first porous membrane having a plurality of holes defined therein sized to permit only gas to pass therethrough; and
an expandable balloon secured about the outer surface of the catheter shaft proximate the distal end of the catheter shaft and coinciding with the inlet vent.

2. The balloon guide catheter according to claim 1, wherein the catheter shaft comprises a formed tubular main liner through which the main lumen extends longitudinally; the catheter shaft further comprising a formed tubular inflation liner through which the inflation lumen extends longitudinally; and the balloon guide catheter further comprises a reinforcing member; wherein the reinforcing member is a braid or coil; and wherein the reinforcing member is disposed about: (i) only the formed tubular main liner; (ii) only assembly of the formed tubular main liner with the first porous membrane; or (iii) assembly of the formed tubular main liner, the first porous membrane and the formed tubular inflation liner.

3. The balloon guide catheter according to claim 1, wherein the inner surface of the catheter shaft has a second exhaust vent defined radially inward in fluid communication between the inflation lumen and the main lumen with a second porous membrane having a plurality of holes defined therein sized to permit only gas to pass therethrough covering the second exhaust vent; the expandable balloon is transitionable between a deflated state and an inflated state; while in the deflated state, the expandable balloon does not block the second exhaust vent.

4. A method for using a balloon guide catheter; wherein the balloon guide catheter has a catheter shaft having an outer surface, a proximal end, and an opposite distal end; the catheter shaft having an inner surface forming a main lumen defined therein extending axially therethrough from the proximal end to the distal end; the main lumen being configured to receive a guidewire therein; the catheter shaft between the inner and outer surfaces having an arc shape inflation lumen defined axially therein arranged semi-encircling the main lumen; the catheter shaft having an inlet vent defined in the outer surface radially outward from the inner surface of the catheter shaft and in fluid communication with the inflation lumen; and the catheter shaft having a first exhaust vent disposed longitudinally through a distal terminating end of the inflation lumen coinciding with a distal terminating end of the main lumen; the balloon guide catheter further including a first porous membrane disposed at the first exhaust vent within the distal terminating end of the inflation lumen; the first porous membrane having a plurality of holes defined therein sized to permit only gas to pass therethrough; and the balloon guide catheter also including an expandable balloon secured about the outer surface of the catheter shaft proximate the distal end of the catheter shaft and coinciding with the inlet vent; the method comprising the steps of:
prior to introduction of the balloon guide catheter into a target vessel, prepping the balloon guide catheter by positively venting residual air distally from the inflation lumen and the expandable balloon via the first exhaust vent.

5. The method according to claim 4, wherein the catheter shaft comprises a formed tubular main liner through which the main lumen extends longitudinally; the catheter shaft further comprising a formed tubular inflation liner through which the inflation lumen extends longitudinally; the balloon guide catheter further comprising a reinforcing member; wherein the reinforcing member is a braid or coil; and wherein the reinforcing member is disposed about: (i) only the formed tubular main liner; (ii) only assembly of the formed tubular main liner with the first porous membrane; or (iii) assembly of the formed tubular main liner, the first porous membrane and the formed tubular inflation liner.

6. The method according to claim 4, wherein the inner surface of the catheter shaft has a second exhaust vent defined radially inward in fluid communication between the inflation lumen and the main lumen with a second porous membrane having a plurality of holes defined therein sized to permit only gas to pass therethrough covering the second exhaust vent; the expandable balloon is transitionable between a deflated state and an inflated state; while in the deflated state, the expandable balloon does not block the second exhaust vent.

7. A method of manufacture of a balloon guide catheter including: a catheter shaft having an outer surface, a proximal end, and an opposite distal end; the catheter shaft having an inner surface forming a main lumen defined therein extending axially therethrough from the proximal end to the distal end; the main lumen being configured to receive a guidewire therein; the catheter shaft between the inner and outer surfaces having an arc shape inflation lumen defined axially therein arranged semi-encircling the main lumen; the catheter shaft having an inlet vent defined in the outer surface radially outward from the inner surface of the catheter shaft and in fluid communication with the inflation lumen; and the catheter shaft having a first exhaust vent disposed longitudinally through a distal terminating end of the inflation lumen coinciding with a distal terminating end of the main lumen and a second exhaust vent defined radially inward through the inner surface of the catheter shaft in fluid communication between the inflation lumen and the main lumen;
a porous membrane disposed at each of the first exhaust vent within the distal terminating end of the inflation lumen and the second exhaust vent; the porous membrane having a plurality of holes defined therein sized to permit only gas to pass therethrough; and an expandable balloon secured about the outer surface of the catheter shaft proximate the distal end of the catheter shaft and coinciding with the inlet vent; the method comprising the step of:
forming a tubular main liner to form the main lumen axially therethrough; the formed tubular main liner having a region etched with a polymeric strike layer at selected sections of surfaces;

punching a first opening radially through the formed tubular main liner that serves as the second exhaust vent disposed radially inward in fluid communication with the main lumen defined axially therethrough;

providing the porous membrane having a region etched with a polymeric strike layer at selected sections of surfaces of the porous membrane;

positioning the porous membrane to cover the punched second exhaust vent defined in the formed tubular main liner; and laminating the formed tubular main liner attached together with the porous membrane under an application of heat.

8. The method according to claim 7, further comprising the step of:

positioning a polymer jacket over the laminated assembly including a mandrel, the formed tubular main liner, and the porous membrane; and applying heat shrink to cause reflow of the polymer jacket bonding the polymer jacket to the region etched with the polymeric strike layer of the porous membrane as well as to the region etched with the polymeric strike layer of the formed tubular main liner.

9. The method according to claim 8, further comprising the steps of forming a tubular inflation liner to form the inflation lumen axially therethrough; the formed tubular inflation liner having a region etched with a polymeric strike layer at selected sections of surfaces;

punching a second opening radially through the formed tubular inflation liner that serves as the inlet vent disposed radially outward in fluid communication with the inflation lumen defined axially therethrough;

positioning the second opening of the formed tubular inflation liner longitudinally relative to the first opening of the formed tubular main liner;

applying at least one outer jacket about the formed tubular inflation liner;

applying heat shrink to cause reflow of the at least one outer jacket forming a fused assembly including a reinforcing member, the formed tubular inflation liner and the formed tubular main liner; and removing the heat shrink prior to attaching the expandable balloon about the fused assembly.

10. The method according to claim 9, wherein prior to the step of positioning the second opening of the formed tubular inflation liner longitudinally relative to the first opening of the formed tubular main liner, further comprising the step of applying the reinforcing member about: (i) the formed tubular main liner, not including the formed tubular inflation liner; (ii) the formed tubular main liner and including the formed tubular inflation liner; or (iii) the formed tubular main liner, wherein a part of the reinforcing member is wrapped about the formed tubular inflation liner, while another part of the reinforcing member is disposed between the formed tubular main liner and the formed tubular inflation liner.

11. The method according to claim 7, wherein the expandable balloon is transitionable between a deflated state and an inflated state; while in the deflated state, the expandable balloon does not block the second exhaust vent.

* * * * *